United States Patent
Sendyureva et al.

(10) Patent No.: US 12,383,482 B2
(45) Date of Patent: Aug. 12, 2025

(54) HAIR COLORING COMPOSITIONS

(71) Applicant: Wella Germany GmBH, Darmstadt (DE)

(72) Inventors: Viktoriya Sendyureva, Frankfurt am Main (DE); Manfred Guenther Schmitt, Bensheim (DE); Frank Veverka, Zwingeberg (DE); Felix Herkner, Eppstein (DE); Bjorn Timo Hoffmann, Darmstadt (DE)

(73) Assignee: Wella Germany GmBH, Darmstadt (DE)

( * ) Notice: Subject to any disclaimer, the term of this patent is extended or adjusted under 35 U.S.C. 154(b) by 118 days.

(21) Appl. No.: 18/254,572

(22) PCT Filed: Nov. 26, 2021

(86) PCT No.: PCT/EP2021/083105
§ 371 (c)(1),
(2) Date: Dec. 11, 2023

(87) PCT Pub. No.: WO2022/112473
PCT Pub. Date: Jun. 2, 2022

(65) Prior Publication Data
US 2024/0024218 A1 Jan. 25, 2024

(30) Foreign Application Priority Data
Nov. 26, 2020 (EP) .................................... 20210145

(51) Int. Cl.
A61Q 5/10 (2006.01)
A61K 8/19 (2006.01)
A61K 8/22 (2006.01)
A61K 8/24 (2006.01)
A61K 8/34 (2006.01)
A61K 8/362 (2006.01)
A61K 8/41 (2006.01)
A61K 8/44 (2006.01)
A61K 8/49 (2006.01)
A61K 8/55 (2006.01)
A61Q 5/12 (2006.01)

(52) U.S. Cl.
CPC ............... *A61K 8/556* (2013.01); *A61K 8/19* (2013.01); *A61K 8/22* (2013.01); *A61K 8/24* (2013.01); *A61K 8/34* (2013.01); *A61K 8/342* (2013.01); *A61K 8/345* (2013.01); *A61K 8/347* (2013.01); *A61K 8/362* (2013.01); *A61K 8/41* (2013.01); *A61K 8/411* (2013.01); *A61K 8/415* (2013.01); *A61K 8/44* (2013.01); *A61K 8/494* (2013.01); *A61Q 5/10* (2013.01); *A61Q 5/12* (2013.01); *A61K 2800/43* (2013.01); *A61K 2800/4322* (2013.01); *A61K 2800/48* (2013.01); *A61K 2800/51* (2013.01); *A61K 2800/882* (2013.01)

(58) Field of Classification Search
CPC . A61K 8/556; A61K 8/19; A61K 8/22; A61K 8/24; A61K 8/34; A61K 8/342; A61K 8/345; A61K 8/347; A61K 8/362; A61K 8/41; A61K 8/411; A61K 8/415; A61K 8/44; A61K 8/494; A61K 2800/43; A61K 2800/4322; A61K 2800/48; A61K 2800/51; A61K 2800/882; A61K 2800/88; A61K 8/365; A61K 8/86; A61Q 5/10; A61Q 5/12
USPC .......................................................... 8/405
See application file for complete search history.

(56) References Cited

U.S. PATENT DOCUMENTS

| | | | |
|---|---|---|---|
| 5,635,167 | A | 6/1997 | Said et al. |
| 7,267,696 | B2 | 9/2007 | Desenne et al. |
| 7,303,588 | B2 | 12/2007 | Desenne et al. |
| 2005/0011017 | A1 | 1/2005 | Legrand et al. |
| 2013/0220358 | A1 | 8/2013 | Agostino et al. |

FOREIGN PATENT DOCUMENTS

| | | |
|---|---|---|
| EP | 1370222 A1 | 12/2003 |
| EP | 1475074 A1 | 11/2004 |
| EP | 1600150 A1 | 11/2005 |
| EP | 1602356 A1 | 12/2005 |
| EP | 1607084 A1 | 12/2005 |
| EP | 1627627 A1 | 2/2006 |
| EP | 1632217 A1 | 3/2006 |
| EP | 2298417 A1 | 3/2011 |
| EP | 3597171 A1 | 1/2020 |
| FR | 2870723 A1 | 12/2005 |
| FR | 2870724 A1 | 12/2005 |
| FR | 2870726 A1 | 12/2005 |
| FR | 2870727 A1 | 12/2005 |
| FR | 2870729 A1 | 12/2005 |

(Continued)

OTHER PUBLICATIONS

International Search Report in connection with PCT/EP2021/083105 issued on Feb. 7, 2022.

(Continued)

*Primary Examiner* — Eisa B Elhilo
(74) *Attorney, Agent, or Firm* — Dennemeyer & Associates LLC

(57) ABSTRACT

It is provided a kit for obtaining a hair coloring composition, a hair coloring composition, and a method for treating hair. The hair coloring composition particularly provides the desired color shade and intensity, together with an enhanced root to tip evenness on hair, particularly on previously colored hair and on hair with a broad range of damage levels along hair length.

16 Claims, No Drawings

(56) References Cited

FOREIGN PATENT DOCUMENTS

| | | |
|---|---|---|
| FR | 2870730 A1 | 12/2005 |
| JP | 2019011293 A | 1/2019 |
| WO | 02078661 A2 | 10/2002 |
| WO | 02089754 A1 | 11/2002 |
| WO | 2009060334 A2 | 5/2009 |
| WO | 2010123866 A2 | 10/2010 |
| WO | 2018053522 A1 | 3/2018 |
| WO | WO 2020188001 A1 * | 9/2020 ............... A61Q 5/10 |

OTHER PUBLICATIONS

Written Opinion of the International Searching Authority in connection with PCT/EP2021/083105 issued on Feb. 7, 2022.
European Search Report in connection with Application No. 20210145.7 issued on May 21, 2021.
International Preliminary Report on Patentability in connection with PCT/EP2021/083105 issued on Mar. 9, 2023.
Notification of Transmittal of the International Preliminary Report on Patentability in connection with PCT/EP2021/083105 issued on Mar. 9, 2023.
Response to Written Opinion of the International Preliminary Examining Authority in connection with PCT/EP2021/083105 filed on Nov. 15, 2022.

* cited by examiner

HAIR COLORING COMPOSITIONS

CROSS-REFERENCE TO RELATED APPLICATIONS

This is a 35 U.S.C. 371 National Stage Patent Application of International Application No. PCT/EP2021/083105, filed Nov. 26, 2021, which claims priority to European application 20210145.7, filed Nov. 26, 2020, each of which is hereby incorporated by reference in its entirety.

TECHNICAL FIELD

The present invention relates to a kit for obtaining a hair coloring composition, a hair coloring composition, a method for treating hair and uses thereof. The hair coloring composition, obtained by mixing a dye component and an oxidative component, has slightly alkaline pH which decreases to slightly acidic pH following its application on hair over development time. The present invention particularly provides the desired color shade and intensity, while maintaining natural strand-to-strand variation together with an enhanced root-to-tip evenness on hair, particularly on previously colored hair and on hair with a broad range of damage levels along hair length.

BACKGROUND

The permanent alteration of the color of keratinous fibers, in particular human hair, by the application of hair dyes is well known. In order to provide the consumer with the hair color, a complex chemical process is sometimes utilized. Permanent hair dyeing formulations typically comprise oxidative hair dye precursors, which can diffuse into the hair through the cuticle and into the cortex where they can then react with each other and suitable oxidizing agents to form the end dye molecules. Due to the larger size of these resultant molecules they are unable to readily diffuse out of the hair during subsequent washing with water and/or detergents; hence delivering a consumer-desired permanency of color.

A great variety of hair oxidative coloring compositions, providing the desired color shade and the desired color intensity, is now available. However, the user is often disappointed with the root-to-tip performance of these compositions. Indeed, especially on previously colored hair, the significant lack of evenness (uniformity) of the coloration may be noticeable between the roots and the tips. Particularly, the tips may be darker than the roots of hair. In addition, these compositions may be aggressive to the hair and cause damages. In order to make composition milder to hair and scalp, its pH may be lowered to slightly alkaline or acidic ranges. However, uniformity issues may be even more pronounced manifesting in virtually no color uptake on virgin hair and excessive color uptake on previously damaged hair, e.g. almost uncolored root hair and oversaturated tips. Another common issue of currently available milder compositions is the high variability in color results from one user to another driven by difference in damage level, which makes final result unpredictable creating dissatisfaction to, both, stylists and final consumers.

There is thus the need for providing a hair coloring composition, obtained by mixing a dye component and an oxidative component, providing a good root-to-tip evenness on hair, particularly on previously colored hair. There is also the need for providing a hair coloring composition, obtained by mixing a dye component and an oxidative component, providing the desired color shade and the desired color intensity, without compromising the root-to-tip evenness on hair. There is also the need for providing a hair coloring composition, obtained by mixing a dye component and an oxidative component, being milder to hair compared to known hair coloring compositions, particularly in terms of pH, preserving natural strand-to-strand variation without compromising the root to tip evenness on hair.

SUMMARY

In one aspect, the present invention relates to a kit for obtaining a hair coloring composition upon the mixing of a dye component and an oxidative component in a weight ratio from 3:1 to 1:3;
  wherein the dye component has a pH from 8.5 to 10, and wherein it comprises, by total weight of the dye component:
    at least one alkalizing agent present in an amount from 0.2 to 4%;
    at least one chelant present in an amount from 1.2 to 1.8%;
    at least one buffering acidic compound present in an amount from 0.01 to 0.6%; wherein the buffering acidic compound is citric acid;
    at least one anionic surfactant present in an amount from 0.2 to 1%;
    at least one fatty alcohol present in an amount from 1.6 to 2.5%;
    at least one non-ionic surfactant present in an amount from 0.1 to 0.5%;
    if present, at least one oxidative hair dye precursor and at least one coupler present altogether in an amount of 20% or less; and
    at least one solvent present in an amount from at least 50%;
  wherein the oxidative component has a pH from 1.8 to 3.5, and wherein it comprises, by total weight of the oxidative component:
    at least one oxidizing agent present in an amount from 1 to 3%;
    at least one buffering acidic compound present in an amount from 0.15 to 0.5%; wherein the buffering acidic compound is phosphoric acid;
    at least one buffering alkali compound present in an amount from 0.2 to 0.6%; wherein the buffering alkali compound is disodium phosphate; and
    at least one solvent present in an amount from at least 50%.

In some embodiments, the hair coloring composition is obtained upon the mixing of a dye component and an oxidative component in a weight ratio from 2:1 to 1:2, preferably of about 1:1.

In some embodiment, the dye component has a pH from 9 to 10, and it comprises, by total weight of the dye component:
  the alkalizing agent present in an amount from 0.2 to 2%, preferably from 0.2 to 1%, preferably from 0.6 to 0.9%;
  the chelant present in an amount from 1.2 to 1.6%, preferably of about 1.4%;
  the buffering acidic compound present in an amount from 0.05 to 0.45%, preferably from 0.15 to 0.45%;
  the anionic surfactant present in an amount from 0.5 to 0.8%, preferably from 0.5 to 0.65%;
  the fatty alcohol present in an amount from 1.6 to 2.3%, preferably from 1.65 to 2.1%;

the non-ionic surfactant present in an amount from 0.2 to 0.3%, preferably of about 0.25%;

the oxidative hair dye precursor and at least one coupler present altogether in an amount from 0.002 to 20%, preferably from 0.002 to 10%, preferably from 0.002 to 4%, preferably from 0.002 to 2%; and the solvent present in an amount from at least 60%, preferably of at least 70%.

In some embodiments, the oxidative component has a pH from 2 to 3, and it comprises, by total weight of the oxidative component:

the solvent present in an amount from at least 60%, preferably of at least 70%;

the oxidizing agent present in an amount from 1.2 to 2.4%, preferably from 1.5 to 2%;

the buffering acidic compound present in an amount from 0.17 to 0.4%, preferably from 0.17 to 0.3%;

the buffering alkali compound present in an amount from 0.2 to 0.5%; preferably from 0.2 to 0.35%; and the solvent present in an amount from at least 60%, preferably of about 70%.

In some embodiments, the alkalizing agent, present in the dye component, is chosen from ammonia, alkanolamines, alkali metals and ammonium hydroxides, alkali metal and ammonium carbonates, and mixtures thereof; preferably from ammonia, monoethanolamine, sodium hydroxide, and mixtures thereof; preferably the alkalizing agent is a mixture of monoethanolamine and sodium hydroxide.

In some embodiments, the chelant, present in the dye component, is chosen from carboxylic acids, phosphonic acids, polyphosphoric acids, their salts thereof, and mixtures thereof; preferably from aminocarboxylic acids; preferably from DTPA, EDDS, EDGA, HPDS, GADS, EDDG, HPDDS, EDTA, EDC, EDDHA, DDS, HBED, their salts thereof, and mixtures thereof; preferably from EDDS, EDTA, their salts thereof, and mixtures thereof; preferably the chelant is a mixture of EDDS and EDTA.

In some embodiments, the buffering acidic compound, present in the dye component, is citric acid.

In some embodiments, the anionic surfactant, present in the dye component, is chosen from C14 to C30 alkyl phosphates, C14 to C30 alkyl ether phosphates, and mixtures thereof; preferably from C14 to C18 alkyl phosphates, C14 to C18 alkyl ether phosphates, and mixtures thereof; preferably the anionic surfactant is a mixture of dicetyl phosphate and ceteth-10 phosphate.

In some embodiments, the fatty alcohol, present in the dye component, is chosen from linear or branched C14 to C30 fatty alcohols; preferably from cetyl alcohol, stearyl alcohol, cetostearyl alcohol, cetearyl alcohol, behenyl alcohols, and mixtures thereof; preferably the fatty alcohol is cetearyl alcohol.

In some embodiments, the non-ionic surfactant, present in the dye component, is chosen from polyoxyethylene C14 to C30 alkyl ethers; preferably from polyoxyethylene C14 to C30 alkyl ethers, comprising one or more polyethyleneoxide chains having at least 50; preferably from steareth-20, steareth-100, steareth-150, steareth-200, and mixtures thereof; preferably the non-ionic surfactant is steareth-200.

In some embodiments, the oxidative hair dye precursor, present in the dye component, is chosen from chosen from toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino) ethyl azanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazol[1,5-a]pyridin-2-yl)oxy] ethanol hydrochloride, salts thereof, and mixtures thereof; and the coupler is chosen from resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene) bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol, and mixtures thereof.

In some embodiments, the solvent, present in the dye component, is chosen from water, or a mixture of water and at least one organic solvent; preferably from C1 to C4 lower alkanols, aromatic alcohols, polyols and polyol ethers, propylene carbonates and mixtures thereof, from ethanol, propanol, isopropanol, glycerol, 1,2-propylene glycol, hexylene glycol, ethoxy diglycol, and mixtures thereof; preferably the solvent is a mixture of water and at least one organic solvent; preferably the solvent is a mixture of water and propylene glycol.

In some embodiments, the oxidizing agent, present in the oxidative component, is chosen from water-soluble inorganic peroxygen materials capable of yielding hydrogen peroxide in an aqueous solution; preferably from hydrogen peroxide, inorganic alkali metal peroxides, organic peroxides, inorganic perhydrate salt bleaching compounds, and mixtures thereof, preferably from hydrogen peroxide, persulphates, and mixtures thereof; preferably the oxidizing component is hydrogen peroxide.

In some embodiments, the buffering acidic, present in the oxidative component, is phosphoric acid.

In some embodiments, the buffering alkali, present in the oxidative component, is disodium phosphate.

In some embodiments, the solvent is chosen from water, or a mixture of water and at least one organic solvent; preferably from C1 to C4 lower alkanols, aromatic alcohols, polyols and polyol ethers, propylene carbonate, and mixtures thereof preferably the solvent is water.

In some embodiments, the dye component further comprises at least one radical scavenger, at least one conditioning agent, at least one direct dye, and/or at least one thickener.

In some embodiments, the oxidative component further comprises at least one chelant, at least one fatty alcohol, at least one conditioning agent, at least one direct dye, and/or at least one thickener.

In some embodiments, the dye component and/or the oxidative component comprises at least one other ingredient chosen from additional anionic surfactants, cationic surfactants, nonionic surfactants, amphoteric surfactants, zwitterionic surfactants, non-thickening viscosity (rheology) modifiers, fragrances, enzymes, dispersing agents, peroxide stabilizing agents, antioxidants, natural ingredients, ceramides, preserving agents, opacifiers and pearling agents, and mixtures thereof.

In a second aspect, the present invention relates to a hair coloring composition, obtained by mixing a dye component and an oxidative component, as described herewith, wherein the hair coloring composition has a pH from 6.8 to 8, preferably from 7.2 to 7.99.

In a third aspect, the present invention relates to a hair coloring composition having a pH from 6.8 to 8, preferably from 7.2 to 7.99, and comprising, by total weight of the composition:
- at least one alkalizing agent present in an amount from 0.1 to 2%;
- at least one oxidizing agent present in an amount from 0.5 to 1.5%;
- at least one chelant present in an amount from 0.6 to 0.9%;
- at least a first buffering acidic compound present in an amount from 0.05 to 0.3%, wherein the first buffering acidic compound is citric acid;
- at least a second buffering acidic compound present in an amount from 0.075 to 0.25%, wherein the second buffering acidic compound is phosphoric acid;
- at least one buffering alkali compound present in an amount from 0.1 to 0.3%, wherein the buffering alkali compound is disodium phosphate;
- a gel network thickener system present in an amount from 1.2 to 4.5%, wherein the gel network thickener system comprises at least one anionic surfactant, at least one fatty alcohol and at least one non-ionic surfactant;
- if present, at least one oxidative hair dye precursor and at least one coupler present altogether in an amount of 10% or less; and
- at least one solvent present in an amount from at least 50%.

In some embodiments, the hair coloring composition further comprises at least one radical scavenger, at least one conditioning agent, at least one direct dye, at least one second chelant and/or at least one thickener.

In some embodiments, the hair coloring composition at least one other ingredient chosen from additional anionic surfactants, cationic surfactants, nonionic surfactants, amphoteric surfactants, zwitterionic surfactants, non-thickening viscosity (rheology) modifiers, fragrances, enzymes, dispersing agents, peroxide stabilizing agents, antioxidants, natural ingredients, ceramides, preserving agents, opacifiers and pearling agents, and mixtures thereof.

In a fourth aspect, the present invention relates to a method of treating hair comprising the steps of:
- providing the dye component and the oxidative component as described herewith;
- mixing the oxidative component and the dye component to obtain a hair coloring composition;
- applying the hair coloring composition for the oxidative dyeing of keratin fibers onto the hair;
- leaving the composition on the hair for from 2 to 60 minutes; and
- rinsing the composition from the hair.

In a fifth aspect, the present invention relates to the use of the hair coloring composition as described herewith, for maintaining natural strand-to-strand variation.

In a fifth aspect, the present invention relates to the use of the hair coloring composition as described herewith, for providing an enhanced root-to-tip evenness on hair.

The inventors have surprisingly shown that the hair coloring compositions, obtained upon mixing a dye component and an oxidative component, according to the invention provide the desired color shade and intensity, without compromising the root-to-tip evenness. Particularly, the hair coloring composition provides an enhanced root-to-tip evenness, even on previously colored hair and on hair with a broad range of damage levels along its length. Unexpectedly, it has been observed that when a coloring composition having a slightly alkaline pH comes in contact with hair, its pH gradually decreases over application time to slightly acidic range. Even bigger pH reduction may be detected on damaged hair. Without wishing to be bound by any theory, the inventors believe that this effect is driven by the specific combination of chelation and buffering. Conventional alkaline hair coloring compositions i.e. having a pH of at least 9 have a sufficient coloration capability, due to the higher amount of alkalizing agent, which, upon reaction with hydrogen peroxide, fast generates high amounts of oxygen required for dyes reaction. When reducing the pH of the hair coloring composition, the speed of the reaction also reduces due to less availability of the oxygen. Color formation may therefore be compromised, which may result in an insufficient intensity and/or an unpredictable color result. In contrast, it is assumed that the chelating agents present in the present hair coloring composition, obtained by mixing a dye component and a tint component, solubilize metals (such as iron or calcium) deposited in smaller amounts on hair root, thereby allowing starting a dye reaction even at slightly alkaline pH. Simultaneously, there is a twofold process on damaged hair, where a lot of copper ions are present, i.e. the chelating agents neutralize copper ions, which make the dye reaction too intensive otherwise, while the buffer capacity of the composition allows lowering pH over application time to slightly acidic pH range and even more than on undamaged hair to avoid excessive colour formation.

DESCRIPTION

As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

By "hair coloring" composition it is meant a composition suitable for changing the color of hair. The hair coloring composition is referred hereinafter as "the composition", unless otherwise specified. The hair coloring composition can comprise oxidative dye precursors, direct dyes or even no, or substantially no, dyes in case of bleaching only compositions where the change of color is mainly caused by the degradation of the natural melanin contained in the hair shaft by the oxidizing agent. The term "hair coloring" composition as used herein covers hair bleaching and hair oxidative dyeing products.

All percentages are by weight of the hair coloring composition, i.e. of the ready-to-use composition, unless otherwise specified. When more than one composition are used during a treatment, the total weight to be considered is the total weight of all the compositions applied on the hair simultaneously (i.e. the weight found "on head"), typically resulting from mixing an oxidative component (also called developer and/or oxidizing component) with a dye component (also called tint, and/or dye component), unless otherwise specified. All ratios or percentages are weight ratios or weight percentages unless specifically stated otherwise.

The term "about", when used in relation to a weight ratio or a weight percentage, means that a specific value should be understood as meaning a range of ±10%. For example, the weight proportion of a compound of about 1%, means a weight proportion ranging from 0.9 to 1.1%. For example, the weight proportion of a compound of about 2.5%, means a weight proportion ranging from 2.25 to 2.75%.

Hair Coloring Composition

It is described a hair coloring composition, obtained upon mixing a dye component and an oxidative component.

Oxidizing Agent

The composition comprises at least one oxidizing agent present in an amount from 0.5 to 1.5%, preferably from 0.6 to 1.2%, preferably about 0.75-1%, by total weight of the composition. "Water-soluble," as defined herein, means that in standard condition at least 0.1 g, 1 g, or 10 g of the oxidizing agent can be dissolved in 1 liter of deionized water.

Prior mixing, the oxidizing agent may be present in the oxidative component in an amount from 1 to 3%, preferably from 1.2 to 2.4%, preferably from 1.5 to 2%, by total weight of the oxidative component.

The oxidizing agents may be water-soluble inorganic peroxygen materials capable of yielding hydrogen peroxide in an aqueous solution; preferably the oxidizing agents may be chosen from hydrogen peroxide, inorganic alkali metal peroxides (such as sodium periodate and sodium peroxide), organic peroxides (such as urea peroxide, melamine peroxide), inorganic perhydrate salt bleaching compounds (such as the alkali metal salts of perborates, percarbonates, perphosphates, persilicates, persulphates), and mixtures thereof; preferably from hydrogen peroxide, persulphates, and mixtures thereof; preferably the oxidizing agent is hydrogen peroxide.

The oxidizing agents can be provided in aqueous solution or as a powder which is dissolved prior to use.

Alkalizing Agents

The composition comprises at least one alkalizing agent present in an amount from 0.1 to 2%, preferably from 0.1 to 1%, preferably from 0.1 to 0.5%, preferably from 0.3 to 0.45%, by weight of the total composition.

Prior mixing, the alkalizing agent is present in the dye component in an amount from 0.2 to 4%, preferably from 0.2 to 2%, preferably from 0.2 to 1%, preferably from 0.6 to 0.9%, by total weight of the dye component.

The alkalizing agents may be chosen from ammonia, alkanolamines (such as monoethanolamine, diethanolamine, triethanolamine, monopropanolamine, dipropanolamine, tripropanolamine 2-amino-2-methyl-1,3-propanediol, 2-amino-1-propanol, 2-amino-2-methyl-1-propanol, and 2-amino-2-hydroxymethyl-1,3-propanediol), dimethylglucamine, guanidium salts, alkali metal and ammonium hydroxides (such as sodium hydroxide), alkali metal and ammonium carbonates, and mixtures thereof; preferably from ammonia, monoethanolamine, sodium hydroxide, and mixtures thereof; preferably the alkalizing agent is a mixture of monoethanolamine and sodium hydroxide.

In the present context, the alkalizing agents (e.g. ammonia, monoethanolamine and their derivatives thereof) are solely classified as "alkalizing agents".

Chelants

The composition comprises at least one chelant present in an amount from 0.6 to %, preferably from 0.6 to 0.8%, preferably 0.7%, by total weight of the composition.

Prior mixing, a chelant is present in the dye component and optionally in the oxidative component. When a chelant is present in the dye component and the oxidative component, the chelant present in the dye component may be referred as the "first chelant" and the chelant present in the oxidative component may be referred as the "second chelant". The first and second chelants respectively present in the dye component and the oxidative component may be the same compounds or may be different compounds.

Prior mixing, a chelant is present in the dye component in an amount from 1.2 to 1.8%, preferably from 1.2 to 1.6%, preferably about 1.4%, by total weight of the dye component.

Prior mixing, if present, a chelant may also be present in the oxidative component in an amount of 0.1% or less, preferably from 0.001 to 0.05%, preferably of about 0.01%, by total weight of the oxidative component.

The chelants may be chosen from carboxylic acids (such as aminocarboxylic acids), phosphonic acids (such as aminophosphonic acids), polyphosphoric acids (such as linear polyphosphoric acids), their salts thereof, and mixtures thereof; preferably from aminocarboxylic acids, aminophosphonic acids, linear polyphosphoric acids, their salts thereof, and mixtures thereof; preferably from aminocarboxylic acids.

Aminocarboxylic acid chelants may be chosen from diethylenetriamine pentaacetic acid (DTPA), ethylenediamine disuccinic acid (EDDS), ethylenediamine diglutaric acid (EDGA), 2-hydroxypropylenediamine disuccinic acid (HPDS), gly cinamide-N,N'-disuccinic acid (GADS), ethylenediamine-N—N'-diglutaric acid (EDDG), 2-hydroxypropylenediamine-N—N'-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalkyldi(sulfosuccinic acids) (DDS), N,N'-bis(2-hydroxybenzyl)ethylenediamine-N,N'-diacetic acid (HBED), their salts thereof, and mixtures thereof; preferably from the group consisting of EDDS, EDTA, their salts thereof, and mixtures thereof.

Aminophosphonic acids may be chosen from aminotri-(methylenephosphonic acid), aminotri-(1-ethylphosphonic acid), aminotri-(isopropylphosphonic acid), ethylene-diamine tetra-(1-ethylphosphonic acid), aminotri-(1-propylphosphonic acid), ethylene-diamine-tetra-(methylenephosphonic acid) (EDTMP), diethylene-triamine-penta-(methylenephosphonic acid) (DTPMP), their salts thereof, and mixtures thereof.

In one embodiment, the (first) chelant present in the dye component is a mixture of EDDS and EDTA.

In one embodiment, the second chelant present in the oxidative component is etidronic acid.

Buffering System

The composition comprises at least one buffering acidic compound present in an amount from 0.08 to 0.55%, preferably from 0.125 to 0.425%, preferably from 0.16 to 0.375%, and at least one buffering alkali compound present in an amount from 0.1 to 0.3%, preferably from 0.1 to 0.25%, preferably from 0.1 0.175%, by total weight of the composition, wherein the buffering acidic compound and the buffering alkali compound form a buffering system. The buffering system enables pH reduction from slightly alkaline to slightly acidic pH.

Prior mixing, the buffering acidic compound may be present in the oxidative component and/or the dye component, preferably in the oxidative component and in the dye component, and the buffering alkali compound may be present in the oxidative component.

Prior mixing, when the buffering acidic compound is present in both the oxidative component and the dye component, the buffering acidic compound is present in an amount from 0.01 to 0.6%, preferably from 0.05 to 0.45%, preferably from 0.15 to 0.45% by total weight of the dye component, and the buffering acidic compound is present in an amount from 0.15 to 0.5%, preferably about 0.17 to 0.4%, preferably 0.17 to 0.3% by total weight of the oxidative component.

Prior mixing, the buffering alkali compound is present in the oxidative component in an amount from 0.2 to 0.6%, preferably from 0.2 to 0.5, preferably from 0.2 to 0.35%, by total weight of the oxidative component.

The buffering acidic compound is chosen from organic and inorganic acids; preferably from sulphurous acid, sulphuric acid, hydrochloric acid, hyponitrous acid, nitrous acid, nitric acid, phosphoric acid, phosphorous acid, citric acid, malic acid, and mixtures thereof preferably from phosphoric acid, phosphorous acid, citric acid, malic acid, hydrochloric acid, hyponitrous acid, and their mixtures; preferably from phosphoric acid, citric acid, and mixtures thereof.

The buffering alkali compound may be chosen from alkali metal salts, amino acids, salts thereof, and mixtures thereof; preferably from glycine, alkali metal salts, amino acids, chlorides, nitrates, salts thereof, and mixtures thereof; preferably from alkali metal of chlorides, nitrates and/or phosphoric acid, glycine, salts thereof, and mixtures thereof; preferably from alkali metal of phosphoric acid, salts thereof, and mixtures thereof preferably the buffering alkali compound is disodium phosphate. In the present context, the alkalizing agents (e.g. ammonia, monoethanolamine, sodium hydroxide, and their derivatives thereof) are not classified as "buffering alkali compounds". The expression "buffering alkali compound" therefore presently excludes e.g. ammonia, monoethanolamine, sodium hydroxide and their derivatives thereof.

The buffer system can comprise a buffering acidic compound being phosphoric acid and citric acid, and a corresponding buffering alkali compound being disodium phosphate.

In one embodiment, the dye component comprises a first buffering acidic compound, and the oxidative component comprises a second buffering alkali compound and a buffering alkali compound. In a preferred embodiment, the first buffering acidic compound is citric acid, the second buffering acidic compound is phosphoric acid and the buffering alkali compound is disodium phosphate.

When the first buffering acidic compound present in the dye component (e.g. citric acid) is different from the second buffering acidic compound present in the oxidative component (e.g. phosphoric acid), the composition comprises from 0.05 to 0.3%, preferably from 0.025 to 0.225%, preferably from 0.075 to 0.225%, of the first buffering acidic compound, and from 0.075 to 0.25%, preferably from 0.0.85 to 0.2%, preferably from 0.085 to 0.15%, of the first buffering acidic compound, by total weight of the composition.

Gel Network Thickener

The composition comprises a gel network thickener system present in an amount from 1.2 to 4.5%, preferably from 2 to 4%, by total weight of the composition. The gel network thickener system is defined as a thickening system comprising a tertiary system. This system comprises at least one anionic surfactant, at least one fatty alcohol and at least one non-ionic surfactant.

Prior mixing, the anionic surfactant component may be present in the dye component, the fatty alcohol may be present in the dye component and/or the oxidative component and the non-ionic surfactant may be present in the dye component.

The anionic surfactant may be chosen from C14 to C30 alkyl phosphates, C14 to C30 alkyl ether phosphates, and mixtures thereof; preferably from C14 to C18 alkyl phosphates, C14-C18 alkyl ether phosphates, and mixtures thereof; preferably the anionic surfactant is a mixture of dicetyl phosphate and ceteth-10 phosphate. Preferably the alkyl ether phosphates have an average of from 1 to 20 and preferably from 1 to 10 ethylene oxide units.

The anionic surfactant may be present in an amount from 0.1 to 0.5%, preferably from 0.25 to 0.4%, preferably from 0.25 to 0.325%, by total weight of the composition.

Prior mixing, the anionic surfactant may be present in the dye component in an amount from 0.2 to 1%, preferably from 0.5 to 0.8%, preferably from 0.5 to 0.65%, by total weight of the dye component.

The fatty alcohol may be chosen from a linear or branched C14 to C30 fatty alcohol, and mixtures thereof; preferably from cetyl alcohol, stearyl alcohol, cetostearyl alcohol, cetearyl alcohol, behenyl alcohols, and mixtures thereof; preferably cetearyl alcohol.

Prior mixing, the fatty alcohol may be present in the dye component and/or the oxidative component. In one embodiment, the fatty alcohol is only present in the dye component. In an alternative embodiment, the fatty alcohol is present in the dye component and in the oxidative component.

The dye component may comprise from 1.6 to 2.5%, preferably from 1.6 to 2.3%, preferably from 1.65 to 2.1% of a fatty alcohol, by total weight of the dye component.

The oxidative component may comprise from 1.6 to 3.4%, preferably 1.8 to 3.2%, preferably from 2 to 3% of a fatty alcohol, by total weight of the oxidative component.

The fatty alcohol may be present in an amount from 0.8 to 1.25%, preferably from to 1.15%, preferably of from 0.825 to 1.05%, by total weight of the composition. Alternatively, the fatty alcohol may be present in an amount from 1.6 to 2.95%, preferably from 1.7 to 2.75%, preferably from 1.825 to 2.55%, by total weight of the composition.

The non-ionic surfactant may be chosen from polyoxyethylene C14 to C30 alkyl ethers; preferably from polyoxyethylene C14 to C30 alkyl ethers, comprising one or more polyethyleneoxide chains having at least 50, or from 50 to 200, or from 100 to 200 ethylene oxide units; preferably from steareth-20, steareth-100, steareth-150, steareth-200, and mixtures thereof; preferably steareth-200.

The non-ionic surfactant may be present in an amount from 0.05 to 0.25%, preferably of about 0.125%, by total weight of the composition.

Prior mixing, the non-ionic surfactant may be present in the dye component in an amount from 0.1 to 0.5%, preferably from 0.2 to 0.3%, preferably of about 0.25%, by total weight of the component.

Hair Dyes

The composition comprises at least one oxidative hair dye precursor (also known as "primary intermediate", "primary dye" or "dyes intermediate") and at least one coupler (also known as "color modifier" or "secondary intermediate") present altogether in an amount of 10% or less, preferably from 0.001 to 10%, preferably from 0.001 to 5%, preferably from 0.1 to 2%, preferably from 0.2 to 1%, by total weight of composition.

Prior mixing, the oxidative hair dye precursor and the coupler may be present altogether in the dye component, in an amount of 20% or less, preferably from 0.002 to 20%, preferably from 0.002 to 10%, preferably from 0.2 to 4%, preferably from 0.4 to 2%, by total weight of component.

The choice of precursors and couplers will be determined by the color, shade and intensity of coloration that is desired. The hair dye precursors and couplers can be used herein, singly or in combination, to provide dyes having a variety of shades ranging from ash blonde to black.

The primary intermediates may be chosen from toluene-2,5-diamine, p-phenylenediamine, N-phenyl-p-phenylene-diamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxy methyl-p-phenylenediamine, 2-(1,2-dihydroxy ethyl)-p-phenylenediamine, 2,2'-(2-(4-aminophenylamino)ethylazanediyl) diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methyl-amino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-di-aminopyrazole sulfate, 4,5-diamino-1-methylpyrazol e, 4,5-diamino-1-ethylpyrazole, 4,5-diamino-1-isopropyl pyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy]ethanol hydrochloride, salts thereof, and mixtures thereof.

The couplers may be chosen from resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethyl aminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 2,4-diaminophenoxy ethanol, 2-amino-4-hydroxyethylaminoanisole, 1,3-bis-(2,4-diaminophenoxy)-propane, 2,2'-(2-methyl-1,3-phenylene)bis(azanediyl) diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methyl-naphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

The oxidative hair dye precursor may be chosen from p-aminophenol, N,N-bis(2-hydroxyethyl)-p-phenylenediamine, 3-methyl-p-aminophenol, methoxymethyl-1,4-diaminobenzene, 2,5-toluenediamine sulfate, and mixtures thereof; and the coupler may be chosen from resorcinol, 4-amino-2-hydroxytoluene, 2-methylresorcinol, hydroxyethyl-3,4-methylenedioxyaniline, and mixtures thereof.

Solvents

The composition comprises at least one solvent, present in an amount of at least 50%, preferably from at least 60%, preferably from at least 70%, by total weight of the composition.

Prior mixing, the solvent may be present in the dye component and/or the oxidative component, preferably in the dye component and in the oxidative component.

Prior mixing, the dye component comprises from at least 50%, preferably from at least 60%, preferably from at least 70%, of a solvent, by total weight of the dye component.

Prior mixing, the oxidative component comprises from at least 50%, preferably from at least 60%, preferably from at least 70%, of a solvent, by total weight of the oxidative component.

The solvent may be selected from water, or a mixture of water and at least one organic solvent to dissolve the compounds that would not typically be sufficiently soluble in water. The organic solvents may be chosen from C1 to C4 lower alkanols (such as ethanol, propanol, isopropanol), aromatic alcohols (such as benzyl alcohol and phenoxyethanol), polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol), propylene carbonate, and mixtures thereof; preferably from the group consisting of ethanol, propanol, isopropanol, glycerol, 1,2-propylene glycol, hexylene glycol, ethoxy diglycol, and mixtures thereof; preferably the organic solvent is propylene glycol.

In one embodiment, the dye component comprises a solvent comprises water and propylene glycol.

In one embodiment, the oxidative component comprises a solvent being water.

pH of Composition

The composition has pH from 6.8 to 8, preferably from 7.2 to 7.99, when freshly mixed (i.e. immediately upon mixing), which over development time on hair drops to 6.5-7.0 (e.g. after 20 min). Slow decomposition of hydrogen peroxide in slightly acidic range results in lower hair damage, but initial slightly alkaline pH allows enough dye formation to deliver desired colour result. Dye formation is known to reduce with the lowering of pH of hair colouring composition, thus, finding the pH range where hair damage is reduced without compromising colour result is important. The pH of the composition can be determined by using either a Mettler Toledo MP220 or a MP225 pH equipment, fitted with a standard laboratory pH electrode. The equipment is calibrated before each use using standard calibration buffers and using standard calibration procedure.

Radical Scavenger

The composition may comprise at least one radical scavenger present in an amount of 0.5% or less, preferably of 0.2% or less, preferably of 0.1% or less.

If present, the composition may comprise from 0.01 to 0.5%, preferably from 0.01 to 0.2%, preferably of about 0.15% %, of at least one radical scavenger, by total weight of the composition.

The dye component may comprise 1% or less, preferably 0.4% or less, preferably 0.2% or less, of at least one radical scavenger, by total weight of the dye component.

Prior mixing, if present, the radical scavenger may be present in the dye component in an amount of 1% or less, preferably from 0.02 to 1%, preferably from 0.02 to 0.4%, preferably of about 0.3%, by total weight of the dye component.

Radical scavengers help to reduce damage to the hair during an oxidative process.

The radical scavengers may be chosen from alkanolamines, amino sugars, amino acids, esters of amino acids, and mixtures thereof preferably from 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, their salts thereof, and mixtures thereof; preferably from glycine, sarcosine, lysine, serine, 2 methoxyethylamine, glucosamine, glutamic acid, morpholine, piperdine, ethylamine, 3 amino-1-propanol, and mixtures thereof. As used herein, the term "salts thereof"—in the context of radical scavengers—means particularly potassium salts, sodium salts, ammonium salts, and mixtures thereof.

Conditioning Agent

The composition may comprise at least one conditioning agent in an amount of 20% or less.

The composition may comprise at least one conditioning agent. If present, the composition may comprise from 0.05 to 20%, preferably from 0.1 to 15%, preferably from 0.2 to 10%, preferably from 0.2% to 5%, preferably about 1.65% or about 2.5% of a conditioning agent, by total weight of the composition.

Prior mixing, the conditioning agent may be present in the dye component, the oxidative component or a third component, preferably the oxidative component.

In one embodiment, the conditioning agent is present in the oxidative component.

Prior mixing, if present, the conditioning agent may be present in the oxidative component in an amount of 40% or less, preferably from 0.1 to 40%, preferably from 0.2 to 30%, preferably from 0.4 to 20%, preferably from 0.4% to 10%, preferably about 3.3%, by total weight of the oxidative component.

The conditioning agents may be chosen from polyhydric alcohol, silicone materials, amino silicones, fatty alcohols, polymeric resins, polyol carboxylic acid esters, cationic polymers, cationic surfactants, insoluble oils, oil-derived materials, mineral oil, and mixtures thereof; preferably the conditioning agent is mineral oil.

Direct Dyes

The composition may also comprise at least one direct dye. The direct dye may be present in an amount from 0.05% to 4%, by total weight of the composition.

Prior mixing, the direct dyes may be present in the dye component and/or the oxidative component.

The dye component may comprise less than 4%, preferably from 0.05 to 4%, of the direct dye, by total weight of the dye component. Alternatively, the dye component may comprise less than 2%, preferably from 0.025 to 2%, of the direct dye, by total weight of the dye component.

The oxidative component may comprise less than 4%, preferably from 0.05 to 4%, of the direct dye, by total weight of the oxidative component. Alternatively, the oxidative component may comprise less than 2%, preferably from 0.025 to 2%, of the direct dye, by total weight of the oxidative component.

Thickeners

The composition may comprise at least one thickener present in an amount of at least 0.05%, preferably from 0.05% to 1.0%, by total weight of the composition.

Prior mixing, the thickener may be present in the dye component and/or in the oxidative component.

Prior mixing, the thickener may be present in the dye component in an amount of at least 0.1%, preferably from 0.1% to 2.0%, preferably about 0.15%, by total weight of the dye component.

Prior mixing, the thickener may be present in the oxidative component in an amount of 0.1% or less, preferably from 0.001% to 0.1%, by total weight of the oxidative component.

The thickeners may be chosen from associative polymers, polysaccharides, non-associative polycarboxylic polymers, and mixtures thereof.

In one embodiment, the dye component comprises at least one polysaccharide.

In one embodiment, the oxidative component comprises at least one associative polymer.

As used herein, the expression "associative polymers" means amphiphilic polymers comprising both hydrophilic units and hydrophobic units, for example, at least one C8 to C30 fatty chain and at least one hydrophilic unit. Associative polymers are capable of reversibly combining with each other or with other molecules. Suitable associative thickeners include, but are not limited to: nonionic amphiphilic polymers comprising at least one hydrophilic unit and at least one fatty-chain unit; anionic amphiphilic polymers comprising at least one hydrophilic unit and at least one fatty-chain unit; cationic amphiphilic polymers comprising at least one hydrophilic unit and at least one fatty-chain unit; and amphoteric amphiphilic polymers comprising at least one hydrophilic unit and at least one fatty-chain unit, and mixtures thereof.

Suitable nonionic amphiphilic polymers comprising at least one fatty chain and at least one hydrophilic unit include, but are not limited to: celluloses modified with groups comprising at least one fatty chain (such as hydroxyethylcelluloses modified with groups comprising at least one fatty chain chosen from alkyl, alkenyl and alkylaryl groups); hydroxypropyl guars modified with groups comprising at least one fatty chain; polyether urethanes comprising at least one fatty chain (such as C8-C30 alkyl or alkenyl groups); copolymers of vinylpyrrolidone and of fatty-chain hydrophobic monomers; copolymers of C1-C6 alkyl acrylates or methacrylates and of amphiphilic monomers comprising at least one fatty chain; copolymers of hydrophilic acrylates or methacrylates and of hydrophobic monomers comprising at least one fatty chain, and mixtures thereof.

Suitable nonionic amphiphilic polymers comprising at least one hydrophilic unit and at least one fatty-chain unit include, but are not limited to: those polymers comprising at least one fatty-chain allyl ether unit and at least one hydrophilic unit comprising an ethylenic unsaturated anionic monomeric unit (such as a vinylcarboxylic acid unit, particularly a unit chosen from units derived from acrylic acids, methacrylic acids, and mixtures thereof), wherein the fatty-chain allyl ether unit corresponds to the monomer of formula (I) below $$CH_2=C(R1)CH_2OB_nR \qquad (I)$$

in which R1 is chosen from H and CH3, B is an ethyleneoxy radical, n is chosen from zero and integers ranging from 1 to 100, R is chosen from hydrocarbon-based radicals chosen from alkyl, alkenyl, arylalkyl, aryl, alkylaryl and cycloalkyl radicals, comprising from 8 to 30 carbon atoms, and, further, for example, from 10 to 24 carbon atoms and even further, for example, from 12 to 18 carbon atoms.

Suitable anionic amphiphilic polymers include, but are not limited to: those polymers comprising at least one hydrophilic unit of unsaturated olefinic carboxylic acid type, and at least one hydrophobic unit of the type such as a (C8-C30) alkyl ester or (C8-C30) oxyethylenated alkyl ester of an unsaturated carboxylic acid, wherein the hydrophilic unit of unsaturated olefinic carboxylic acid type corresponds to, for example, the monomer of formula (II) below $$CH_2=C(R1)COOH \qquad (II)$$

in which R1 is chosen from H, CH3, C2H5 and CH2COOH (i.e. acrylic acid, methacrylic, ethacrylic and itaconic acid units); and wherein the hydrophobic unit of the type such as a (C8-C30) alkyl ester or (C8-C30) oxyethylenated alkyl ester of an unsaturated carboxylic acid corresponds to, for example, the monomer of formula (III) below $$CH_2=C(R1)COOB_nR2 \qquad (III)$$

in which R1 is chosen from H, CH3, C2H5 and CH2COOH (i.e. acrylate, methacrylate, ethacrylate and itaconate units), B is an ethyleneoxy radical, n is chosen from zero and integers ranging from 1 to 100, R2 is chosen from C8-C30 alkyl radicals, for example, C12-C22 alkyl radical.

Anionic amphiphilic polymers may further be cross-linked. The crosslinking agent can be a monomer comprising a group (IV) below:

$$CH_2=C< \qquad (IV)$$

with at least one other polymerizable group whose unsaturated bonds are not conjugated with respect to one another. Mention may be made, for example, of polyallyl ethers such as polyallylsucrose and polyallyl pentaerythritol.

Suitable cationic amphiphilic polymers include, but are not limited to: quaternized cellulose derivatives and polyacrylates comprising amino side groups. The quaternized cellulose derivatives are, for example, chosen from quaternized celluloses modified with groups comprising at least one fatty chain, such as alkyl, arylalkyl and alkylaryl groups comprising at least 8 carbon atoms, and mixtures thereof, quaternized hydroxyethylcelluloses modified with groups comprising at least one fatty chain, such as alkyl, arylalkyl and alkylaryl groups comprising at least 8 carbon atoms, and mixtures thereof. The alkyl radicals borne by the above quaternized celluloses and hydroxyethylcelluloses, for example, contain from 8 to carbon atoms. The aryl radicals, for example, are chosen from phenyl, benzyl, naphthyl and anthryl groups.

Suitable amphoteric amphiphilic polymers comprising at least one hydrophilic unit and at least one fatty-chain unit, may be made, for example, of methacrylamidopropyltrimethylammonium chloride/acrylic acid/C8-C30 alkyl methacrylate copolymers, wherein the alkyl radical is, for example, a stearyl radical.

Preferred associative polymers comprise at least one hydrophilic unit which is unsaturated carboxylic acid or its derivatives, and at least one hydrophobic unit which is a C8 to C30 alkyl ester or oxyethylenated C8-C30 alkyl ester of unsaturated carboxylic acid. The unsaturated carboxylic acid is preferably acrylic acid, methacrylic acid or itaconic acid. Commercially available materials include those sold as Aculy-22 by Rohm & Haas; Permulen TR1, Carbopol 2020, Carbopol Ultrez-21 by Noveon, Structure 2001/3001 by National Starch. Other preferred associative polymers include polyether polyurethane, commercially available as Aculyn-44/-46 by Rohm and Haas. Further preferred associative polymers include cellulose modified with groups comprising at least one C8-C30 fatty chain, commercially available under the trade name Natrosol Plus Grade 330 CS by Aqualon.

Suitable non-associative cross-linked polycarboxylic polymers include, but are not limited to: cross-linked acrylic acid homopolymers, copolymers of acrylic or (meth)acrylic acid and of C1-C6 alkyl acrylate or (meth)acrylate, and mixtures thereof. Commercially available materials include those sold as Carbopol 980/981/954/2984/5984 by Noveon, Synthalen M/Synthalen L/Synthalen K by 3V Sigma, Aculyn-33 by Rohm and Haas.

The polysaccharides may be chosen from glucans, modified and unmodified starches, amylose, amylopectin, glycogen, dextrans, celluloses and derivatives thereof, mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans, xanthan gums, gellan gums, welan gums, scleroglucans, succinoglycans, and mixtures thereof; preferably from the group consisting of xanthan gum, gellan gum, welan gum, scleroglucan or succinoglycan, and mixtures thereof, preferably from the group consisting of xanthan gum, succinogylcan, and mixtures thereof; preferably the polysaccharide is xanthan gum.

Other Ingredients

The composition according to the present invention may comprise, in addition to the ingredients indicated above, further ingredients in order to further enhance the properties of the composition, as long as these are not excluded by the claims. The composition may comprise 7% or less, preferably from 0.01 to 7%, of ingredients, other than those described above, by total weight of the composition.

Prior mixing, the other ingredients may be present in the dye component and/or in the oxidative component.

The dye component may comprise 5% or less, preferably from 0.01 to 5%, of the ingredients, by total weight of the dye component.

The oxidative component may comprise 5% or less, preferably from 0.01 to 5%, of the other ingredients, by total weight of the oxidative component.

The other ingredients may be chosen from additional anionic surfactants (e.g. sodium cetearyl sulfate), cationic surfactants, nonionic surfactants, amphoteric surfactants, zwitterionic surfactants, non-thickening viscosity (rheology) modifiers (e.g. sodium sulfate), fragrances, enzymes, dispersing agents, peroxide stabilizing agents (e.g. salicylic acid), antioxidants (e.g. ascorbic acid, sodium sulfite and mixture thereof), natural ingredients, ceramides, preserving agents, opacifiers and pearling agents, and mixtures thereof. Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

The dye component may comprise at least one antioxidant.

In one embodiment, the dye component comprises from 0.1 to 2%, preferably from to 1.5%, preferably about 0.7%, of the antioxidant, by total weight of the dye component. The hair coloring composition may comprise from 0.0.5 to 1%, preferably from 0.25 to %, preferably about 0.35%, of the antioxidant, by total weight of the dye component.

The antioxidant may be chosen from ascorbic acid, sodium sulfite, and mixture thereof; preferably the antioxidant is a mixture of ascorbic acid and sodium sulfite.

The dye component may comprise at least one non-thickening viscosity modifier.

In one embodiment, the dye component comprises from 0.5 to 1.5%, preferably from 0.7 to 1.3%, preferably about 1%, of the non-thickening viscosity modifier, by total weight of the dye component. The hair coloring composition may comprise from 0.25 to 0.75%, preferably from 0.35 to 0.65%, preferably about 0.5%, of the non-thickening viscosity modifier, by total weight of the dye component.

The non-thickening viscosity modifier may be sodium sulfate.

The oxidative component may also comprise at least one peroxide stabilizing agent.

In one embodiment, oxidative component comprises from 0.01 to 0.5%, preferably from 0.05 to 0.2%, preferably about 0.1%, of the peroxide stabilizing agent, by total weight of the oxidative component. The hair coloring composition may comprise from 0.005 to 0.25%, preferably from 0.025 to 0.1%, preferably about 0.0.5%, of the peroxide stabilizing agent, by total weight of the dye component.

The peroxide stabilizing agent may be salicylic acid.

The oxidative component may also comprise an additional surfactant, particularly when the oxidative component also comprises a fatty alcohol e.g. cetearyl alcohol.

The oxidative component may comprise from 0.7 to 1.7%, preferably from 0.9 to 1.5%, preferably about 1.2%, of the additional surfactant, by total weight of the oxidative component. The hair coloring composition may comprise from 0.35 to 0.85%, preferably from 0.45 to 0.75%, preferably about 0.6%, of the additional surfactant, by total weight of the oxidative component.

The additional surfactant may be chosen from alkyl sulfates, polyoxyethylene ethers, preferably sodium cetearyl sulfate.

Mixing of a Dye Component and an Oxidative Component

The hair coloring composition, as described herein, is obtained by mixing a dye component and an oxidative component in a weight ratio from 3:1 to 1:3, preferably from 2:1 to 1:2, preferably of about 1:1. The hair coloring composition corresponds to the ready-to-use composition i.e. to the composition ready to be applied onto hair. The dye component and the oxidative component may be mixed just before applying the hair coloring composition onto hair.

The oxidative component may comprise the oxidizing agent, the second buffering acidic compound, the buffering alkali compound, the fatty alcohol (gel network), the solvent, optionally the second chelant, optionally the conditioning agent and optionally the direct dyes.

The oxidative component may have a pH from 1.8 to 3.5, preferably from 2 to 3.

The dye component may comprise the chelant, the first buffering acidic compound, the anionic surfactant (gel network), the fatty alcohol (gel network), the non-ionic surfactant (gel network), the alkalizing agent, the hair dye precursor, the coupler, the solvent, optionally the conditioning agent, optionally the direct dyes and optionally the thickener.

The dye component may have a pH from 8.5 to 10, preferably from 9 to 10.

Method of Use/Kits

It is described a kit for obtaining a hair coloring composition, comprising at least one dye component, at least one oxidative component, optionally at least one conditioning component, optionally a pre-treatment composition and/or optionally a colour refresher composition.

The dye component and the oxidative component are described hereinbefore.

The kit for obtaining a hair coloring composition upon mixing a dye component and an oxidative component in a weight ratio from 3:1 to 1:3, preferably from 2:1 to 1:2, preferably of about 1:1; ( . . . ).

The compounds/ingredients correspond to the compounds/ingredients described above.

Retail oxidative hair dye compositions are usually sold in kits comprising, in individually packaged components such as separate containers, a dye component (also called "dye cream" for emulsions or "dye liquid" for solutions) comprising the oxidative dye precursors and alkalizing agent which is typically ammonia in a suitable carrier and; a oxidative component (also called "hydrogen peroxide cream" for emulsions or "hydrogen peroxide liquid" for solutions) comprising the oxidizing agent (usually hydrogen peroxide). The consumer mixes the dye component and oxidizing component together immediately before use and applies it onto the hair. Similarly, retail bleaching compositions are also usually sold as a kit comprising two or three individually packaged components typically in two or three separate containers. The first component comprises the ammonium ion source (e.g. ammonia), the second component comprises the oxidizing agent and the third (optional) component comprises a second oxidizing agent. The bleaching compositions are obtained by mixing the above-mentioned compositions immediately before use.

For, the professional hair salon market, the hair dye component and the oxidizing component and/or bleaching compositions are typically supplied independently to allow the professional to select a preferred combination.

After working the combined mixture for a few minutes (to insure uniform application to all of the hair), the oxidative dye composition is allowed to remain on the hair for an amount sufficient for the dyeing to take place (usually from 2 to 60 minutes, typically 30 to 45 minutes). The consumer or salon professional then rinses the hair thoroughly with water and/or shampoo and allows it to dry. It will be observed that the hair has changed from its original colour to the desired colour.

In both retail and professional applications, an optional conditioning agent (conditioning component) can also be provided. In this embodiment, all three compositions can be mixed immediately before use and applied together, or the conditioning agent can be applied (after an optional rinse step), as a post-treatment immediately after the oxidative dye composition or bleaching composition resulting from the mixture of the other containers.

The kits may also comprise as optional components a pre-treatment composition and/or a colour refresher composition. Such colour refresher compositions comprise at least one pre-formed dye and may be applied to the hair immediately after the oxidative colour i.e. from 1 minute after oxidative hair dye or bleach application to 60 days after the application. These colour refresher compositions can be used to increase the initial colour obtained and or boost the colour during the wash and style cycle until the next oxidative colouring or bleaching event.

Packaging and Dispensing Devices

The present invention may be provided in a variety of packaging devices and/or dispensing devices. These dispensing devices can come in the form of separate devices which may be used independently or in combination with one another. Typically, the hair colouring or bleaching compositions are contained within separate single or multi compartment containers so that the compositions can be stored separately from one another before use. The compositions are then mixed together by a mixing means and then dispensed from the device and applied to the consumer's hair by an application means.

The most common packaging device which can be used for the present invention involves storing the developer in a container such as a bottle, tube, aerosol, or a sachet and separately storing the dye lotion in an additional compartment within the developer container or preferably in a separate container which may be identical such as a dual sachet or aerosol systems for example or different such as a bottle and tube system. Any combination may be used and is typically contingent on the type of composition being stored i.e. whether or not it is a thick or thin type. The consumer or hair salon professional may mix the oxidizing component and the dye component by any means. This may simply involve the use of a mixing bowl into which the compositions are dispensed and then mixed, preferably using a mixing means such as a tool. Alternatively, it may involve the addition of one of the compositions into the container of the other composition (typically the dye composition is added to the oxidizing composition), followed by manual shaking or mixing with a tool. Another system involves the perforation or displacement of a seal located between the separate compartments of the dye and oxidizing composition within a single container or sachet followed by manual mixing within the container or in a separate and or additional container.

The devices described herein above can also be used in combination with a product delivery and or application tool to aid application of the product onto the hair. Again these devices may be of a very simple nature such as a nozzle attached to one of the containers or a separate applicator device such as a comb or brush. Such combs and brushes can be adapted in order to achieve particular effects, whether it may be quick and even coverage or root/hairline touch up, or highlights or streaks. Alternatively, the container or one of the containers may be provided with a comb attached to or instead of the dispensing nozzle whereby the product is dispensed through hollow tines and dispensing apertures located in the comb tines. The comb tines may be provided with single or multiple openings along the tines to improve product application and evenness especially root to tip. Product dispensation can be achieved by mechanical pressure applied to the container for example delaminating bottles or any of the mechanisms described hereinabove. The comb may be provided on the container such as to facilitate easy application and may be positioned vertically (so called verticomb) or at an angle to allow the consumer to access all areas. All devices may be designed to have inter-changeability, so that a range of different tools for hair application can be provided to the consumer.

The application devices may also include devices which assist in achieving particular effects such as highlighting such as highlighting combs, brushes and tools, foils and highlighting caps. Highlighting devices comprising a hinged device into which an amount of composition is placed and then used to apply the composition to pre-determined/selected hair strands may also be used.

Method of Hair Dyeing

In a third aspect, the present relates to a method of treating hair with the composition may therefore comprise the steps of:

a) providing a dye component as described herein;
b) providing an oxidative component as described herein;
c) mixing the oxidative component and the dye component to obtain a hair coloring composition as described herein;
d) applying the hair coloring composition for the oxidative dyeing of keratin fibers onto the hair;
e) leaving the composition on the hair for from 2 to 60 minutes; and
f) subsequently rinsing the composition from the hair.

The hair coloring composition may be obtained by mixing immediately prior to use a dye component and the oxidative component. A sufficient amount of the mixture is applied to the hair, according to the hair abundance, generally from 60 to 250 grams. Upon such preparation the composition is applied to the hair to be dyed and remains in contact with the hair for an amount of time effective to dye the hair. Typically, the hair coloring composition is allowed to act on the hair from 2 to 60, preferably 10 to 30, preferably 20 minutes, at a temperature ranging from 15 to 50° C. Thereafter, the hair is rinsed with water to remove the composition and dried. If necessary, the hair is washed with a shampoo and rinsed, e.g., with water or a weakly acidic solution, such as a citric acid or tartaric acid solution, and dried. Optionally, a separate conditioning product may also be provided.

The method may further comprise waiting a period of time, typically between 2 minutes and 60 minutes, and then rinsing the hair coloring composition from the hair. The hair coloring composition can be applied on hair via applicator bottle or brush. It can be used on full head or partly on single strands (highlight application) as common highlight applicator foils, caps and special applicators can be used, but also freehand techniques such as balayage, with brush and/or combs can be possible. The composition can also be applied as a mousse via a manual spray, a pressurized container or an aerosol mousse. The composition may be dispensed as a solid form to which water is added to generate the oxidant and form a thickened vehicle suitable for hair coloring.

EXAMPLES

The following examples illustrate the hair coloring compositions according to the present disclosure. It is understood that the examples and embodiments described herein are for illustrative purposes only and that various modifications or changes in light thereof will be suggested to one skilled in the art without departing from the scope of the present disclosure.

Method for Treating Hair

In all examples, the oxidative component and the dye component are mixed together in 1:1 mixing ratio either in a bowl or a bottle. Compositions are applied on hair of a model so that one composition is applied on one side and another composition is applied on another side. Application is by two stylists in parallel in order to exclude time difference effect on final result. Compositions are left for 20 min to develop, then thoroughly rinsed off Subsequently, hair are washed with shampoo and blow dried.

Assessment of the Root-to-Tip Evenness (Color Uniformity)

Assessment of the root-to-tip evenness is done by trained and calibrated stylists. For the first step, roots, mids and tips are compared so that roots coloured with the first composition are compared to roots coloured with the second composition. For the second step, models' hair are folded in a way to hold the tips next to the roots on both sides in order to have comparison of the colour difference of different hair portions for both compositions simultaneously. For the second part sides, the assessment is done using a scale from "a" (first composition is obviously worse than the second composition) to "g" (first composition is obviously better than the second composition).

Hair Coloring Compositions A and B

It is provided a dye component A1 and an oxidative component A2, as respectively shown in tables 1 and 2 below, which are mixed at a weight 1:1 ratio for providing a hair coloring composition A according to the present invention.

It is also provided a dye component B1 and an oxidative component B2, as respectively shown in tables 1 and 2 below, which are mixed at a weight 1:1 ratio for providing a reference hair coloring composition B.

The proportions in the tables 1 and 2 are per total weight of the component.

TABLE 1

| Materials | A1 | B1 |
|---|---|---|
| Dicetyl phosphate, ceteth-10 phosphate | 0.50-0.70 | 0.50-0.70 |
| Cetearyl alcohol | 1.60-2.20 | 1.60-2.20 |
| Steareth-200 | 0.10-0.50 | 0.10-0.50 |
| Sodium hydroxide | 0.05-0.25 | 0.05-0.25 |
| Polysaccharide | 0.10-0.50 | 0.10-0.50 |
| Polyol | 5.00-6.50 | 5.00-6.50 |
| Pigment | 0.50 | 0.50 |
| Ascorbic acid | 0-0.40 | 0-0.40 |
| Sodium sulfite anhydrous | 0-0.40 | 0-0.40 |
| Disodium EDTA | 0.10 | 0.10 |
| Citric acid, anhydrous | 0.2 | 0.2 |
| 2-methoxymethyl-p-phenylenediamine | 0.150 | 0.150 |
| 1-hydroxyethyl 4,5-diamino pyrazole sulfate | 0.240 | 0.240 |
| 1-naphthol | 0.145 | 0.145 |
| Resorcinol | 0.110 | 0.110 |
| 4-amino-2-hydroxytoluene | 0.110 | 0.110 |
| Trisodium ethylenediamine disuccinate (37%) | 3.40 | 1.70 |
| Monoethanolamine | 0.40-1.00 | 0.40-1.00 |
| Fragrance | 0-0.50 | 0-0.50 |
| Water | Q.s. 100 | Q.s. 100 |

TABLE 2

| Materials | A2 | B2 |
|---|---|---|
| Conditioning agent | 0-1.00 | 0-1.00 |
| Cetearyl alcohol | 2.00-4.00 | 2.00-4.00 |
| Sodium cetearyl sulfate | 0.50-1.50 | 0.50-1.50 |
| Disodium phosphate, anhydrous | 0.35 | 1.5 |
| Salicylic acid | 0-0.2 | 0-0.2 |
| Etidronic acid | 0.01-0.1 | 0.01-0.1 |
| Hydrogen peroxide max. 49.9% | 3.8 | 3.8 |
| Orthophosphoric Acid, 85% in water | 0.35 | 1.75 |
| Water | Q.s. 100 | Q.s. 100 |

Hair Coloring Compositions C and D

It is provided a dye component C1 and an oxidative component C2, as respectively shown in tables 3 and 4 below, which are mixed at a weight 1:1 ratio for providing a hair coloring composition C according to the present invention.

It is also provided a dye component D1 and an oxidative component D2, as respectively shown in tables 3 and 4 below, which are mixed at a weight 1:1 ratio for providing a reference hair coloring composition D.

The proportions in the tables 3 and 4 are per total weight of the component.

TABLE 3

| Materials | C1 | D1 |
|---|---|---|
| Dicetyl phosphate and ceteh-10 phosphate | 0.50-0.70 | 0.50-0.70 |
| Cetearyl alcohol | 1.60-2.20 | 1.60-2.20 |
| Steareth-200 | 0.10-0.50 | 0.10-0.50 |
| Sodium hydroxide | 0.25-0.50 | 0.25-0.50 |
| Acrylate | 0.50-1.00 | 0.50-1.00 |
| Polyol | 6.50-8.00 | 6.50-8.00 |
| Pigment | 0.75 | 0.75 |
| Ascorbic acid | 0-0.40 | 0-0.40 |
| Sodium sulfite anhydrous | 0-0.40 | 0-0.40 |
| Disodium EDTA | 0.10 | 0.10 |
| Citric acid anhydrous | 0.40 | 0.40 |
| Sodium sulfate, anhydrous | 1.00 | 1.00 |
| 2-methoxymethyl-p-phenylenediamine | 0.075 | 0.075 |
| 1-hexyl 4,5-diamino pyrazole sulfate | 0.105 | 0.105 |
| 2,4-diaminophenoxyethanol, HCL | 0.12 | 0.12 |
| 4-amino-2-hydroxytoluene | 0.055 | 0.055 |
| Trisodium ethylenediamine disuccinate (37%) | 3.40 | 1.70 |
| Monoethanolamine | 0.80-1.20 | 0.80-1.20 |
| Fragrance | 0.35 | 0.35 |
| Water | Q.s. 100 | Q.s. 100 |

TABLE 4

| Materials | C2 | D2 |
|---|---|---|
| Disodium phosphate, anhydrous | 0.2 | 1.5 |
| Salicylic acid | 0.01-0.5 | 0.01-0.5 |
| Etidronic acid | 0.01-0.5 | 0.01-0.5 |
| Hydrogen peroxide max. 49.9% | 2.00-6.00 | 2.00-6.00 |
| Orthophosphoric acid, 85% in water | 0.2 | 1.75 |
| Thickener | 0.5-1.0 | 0.5-1.0 |
| Water | Q.s. 100 | Q.s. 100 |

Results

The performance of each hair coloring compositions are on two models and the uniformity of the coloration (root-to-tip evenness) is by a professional hairdresser. The hairdresser compares the uniformity of the coloration of the hair coloring compositions according to the invention (A or C) in comparison with the reference hair coloring compositions (B or D), using the following scale: a (obviously worse), b (noticeably worse), c (slightly worse), d (equal), e (slightly better), f (noticeably better) and g (obviously better). In both cases, for each model, the hairdresser assesses that the uniformity of the coloration is noticeably better (f) for the hair coloring composition according to the invention (A or C) in comparison with the reference hair coloring composition (B or D).

In addition, the hair coloring composition according to the invention (A or C) exhibits brighter and overall significantly more intensive color in comparison with the reference hair coloring composition (B or D).

Hair Coloring Composition E

It is provided a dye component E1 and an oxidative component E2, as respectively shown in tables 5 and 6 below, which are mixed at a weight 1:1 ratio for providing a hair coloring composition E according to the present invention.

The proportions in the tables 5 and 6 are per total weight of the component.

TABLE 5

| Materials | E1 |
|---|---|
| Dicetyl phosphate | 0.37 |
| Ceteth-10 phosphate | 0.29 |
| Cetearyl alcohol | 2.10 |
| Steareth-200 | 0.25 |
| Sodium hydroxide | 0.10 |
| Xantham gum | 0.15 |
| Propylene glycol | 8.00 |
| Mica | 0.42 |
| Titanium oxide | 0.07 |
| Ascorbic acid | 0.30 |
| Sodium sulfate | 1.00 |
| Sodium sulfite | 0.40 |
| Disodium EDTA | 0.10 |
| EDDS | 1.31 |
| Citric acid, anhydrous | 0.20 |
| Dyes | — |
| Monoethanolamine | 0.50 |
| Fragrance | 0.30 |
| Water | Q.s. 100 |

TABLE 6

| Materials | E2 |
|---|---|
| Mineral oil | 3.30 |
| Cetearyl alcohol | 2.00 |
| Sodium cetearyl sulfate | 0.80 |
| Disodium phosphate | 0.35 |
| Salicylic acid | 0.10 |
| Etidronic acid | 0.01 |
| Hydrogen peroxide | 2.00 |
| Phosphoric acid | 0.30 |
| Water | Q.s. 100 | pH Control on Hair Application

The hair coloring composition E, obtained by mixing the dye component E1 and the oxidative component E2, according to the present invention, is particularly suitable for application on hair, as the pH of the hair coloring composition only evolves from a slight alkaline pH (upon application) to a slight acidic (after 20 min), as shown in table 7 below. Maintaining a gradual reduction of the pH of the hair coloring composition from a slightly alkaline pH to a slightly acidic pH is particularly wanted, as slightly alkaline pH enables desired color formation, while pH reduction to slightly acidic range ensures less damage and less overdeposition of dyes on damaged hair.

TABLE 7

| Test E (E1 + E2) | pH in the bowl | pH on hair upon application | pH on hair after 20 min |
|---|---|---|---|
| 1 | 7.42 | 7.18 | 6.85 |
| 2 | 7.42 | 7.16 | 6.90 |
| 3 | 7.42 | 7.18 | 6.90 |
| 4 | 7.42 | 7.19 | 7.00 |

The inventors have tested different buffering systems of reference (watery oxidative components) for demonstrating the difference of pH of hair, by mixing the dye component E1 with four different oxidative components i.e. component E2A (invention) and components E2B-D (comparison), as shown in the table 8 below, before application on untreated hair (no pre-treatment with bleach).

TABLE 8

|  | E2A | E2B | E2C | E2D |
|---|---|---|---|---|
| Disodium phosphate | 0.35 | 0.08 | 2.00 | 1.00 |
| Phosphotic acid (85%) | 0.35 | 0.10 | 3.00 | 1.10 |
| Hydrogen peroxide | 2.00 | 2.00 | 2.00 | 2.00 |
| Water | q.s. | q.s. | q.s. | q.s. |
| pH | 2.89 | 2.74 | 2.07 | 2.59 |

The results obtained are shown in the table 9 below.

TABLE 9

| Composition | Tests | pH in the bowl | pH on hair upon application | pH on hair after 20 min |
|---|---|---|---|---|
| EA (E1 + E2A) | 1 | 7.26 | 7.23 | 6.90 |
| | 2 | 7.26 | 7.24 | 6.87 |
| | 3 | 7.26 | 7.25 | 6.99 |
| | 4 | 7.26 | 7.25 | 7.01 |
| EB (E1 + E2B) | 1 | 8.98 | 8.85 | 7.31 |
| | 2 | 8.98 | 8.88 | 7.33 |
| | 3 | 8.98 | 8.78 | 7.77 |
| | 4 | 8.98 | 8.81 | 7.70 |
| EC (E1 + E2C) | 1 | 4.12 | 4.19 | 4.52 |
| | 2 | 4.12 | 4.20 | 4.43 |
| | 3 | 4.12 | 4.23 | 4.48 |
| | 4 | 4.12 | 4.23 | 4.50 |
| ED (E1 + E2D) | 1 | 6.18 | 6.16 | 5.97 |
| | 2 | 6.18 | 6.17 | 5.97 |
| | 3 | 6.18 | 6.17 | 6.11 |
| | 4 | 6.18 | 6.18 | 6.12 |

As shown by the data reported in table 9 above, only the composition EA (E1+E2A) (invention) provides a satisfactory pH on hair, from a slightly alkaline pH upon application to a slightly acidic pH after 20 min, thereby providing, in combination with the chelant, the desired color shade and intensity, while maintaining natural strand-to-strand variation together with an enhanced root-to-tip evenness on hair and less hair damage.

The inventors have also tested the composition EA (E1+E2A) on bleached hair. The results obtained are shown in the table 10 below.

TABLE 10

| Composition | Tests | pH in the bowl | pH on hair upon application | pH on hair after 20 min |
|---|---|---|---|---|
| EA (E1 + E2A) | 1 | 7.26 | 7.21 | 6.93 |
| | 2 | 7.26 | 7.23 | 6.98 |
| | 3 | 7.26 | 7.21 | 6.98 |
| | 4 | 7.26 | 7.21 | 7.03 |

As shown by the data reported in tables 9 and 10 above, the effects of the composition EA (E1+E2A) (invention) does not significantly vary when applied to untreated hair and bleached hair.

Hair Coloring Composition F

It is provided a dye component F1 and an oxidative component F2, as respectively shown in tables 11 and 12 below, which are mixed at a weight 1:1 ratio for providing a hair coloring composition F according to the present invention.

The proportions in the tables 11 and 12 are per total weight of the component.

TABLE 11

| Materials | F1 |
|---|---|
| Dicetyl phosphate | 0.29 |
| Ceteth-10 phosphate | 0.23 |
| Cetearyl alcohol | 1.68 |
| Steareth-200 | 0.20 |
| Sodium hydroxide | 0.25 |
| Xantham gum | 0.15 |
| Propylene glycol | 5.00 |
| Mica | 0.42 |
| Titanium oxide | 0.07 |
| Ascorbic acid | 0.30 |
| Sodium sulfate | 1.00 |
| Sodium sulfite | 0.40 |
| Disodium EDTA | 0.10 |
| EDDS | 1.31 |
| Citric acid, anhydrous | 0.45 |
| 2-Methoxymethy-p-Phenylendiamine | 0.35 |
| 1-HYDROXYETHYL 4,5-DIAMINO PYRAZOLE SULFATE | 0.95 |
| p-Aminophenol | 0.50 |
| N,N-Bis(2-Hydroxyethyl)-p-Phenylenediamine Sulfate | 0.10 |
| 2-Methylresorcinol | 0.50 |
| 4-Amino-2-Hydroxytoluene | 1.00 |
| Monoethanolamine | 0.99 |
| Fragrance | 0.30 |
| Water | Q.s. 100 |

TABLE 6

| Materials | F2 |
|---|---|
| Mineral oil | 5.00 |
| Cetearyl alcohol | 3.00 |
| Sodium cetearyl sulfate | 1.20 |
| Disodium phosphate | 0.20 |
| Salicylic acid | 0.10 |
| Etidronic acid | 0.01 |
| Hydrogen peroxide | 2.00 |
| Phosphoric acid | 0.17 |
| Water | Q.s. 100 |

The hair coloring composition F, obtained by mixing the dye component F1 and the oxidative component F2, according to the present invention, is particularly suitable for application on hair, as the pH of composition only evolves from a slight alkaline pH (upon application) to a slight acidic (after 20 min) the way it has been demonstrated before with hair coloring composition F.

EMBODIMENTS

Embodiment 001: A kit for obtaining a hair coloring composition upon the mixing of a dye component and an oxidative component in a weight ratio from 3:1 to 1:3.

E002: A kit according to embodiment 001, wherein the dye component and the oxidative component are mixed in a weight ratio from 2:1 to 1:2.

E003: A kit according to E001-002, wherein the dye component and the oxidative component are mixed in a weight ratio of about 1:1.

E004: A kit according to E001-003, wherein the dye component has a pH from 8.5 to 10.

E005: A kit according to E001-004, wherein the dye component has a pH from 9 to 10.

E006: A kit according to E001-005, wherein the oxidative component has a pH from 1.8 to 3.5.

E007: A kit according to E001-006, wherein the oxidative component has a pH from 2 to 3.

E008: A kit according to E001-007, wherein the dye component comprises at least one alkalizing agent.

E009: A kit according to E008, wherein the dye component comprises from 0.2 to 4% of the alkalizing agent, by total weight of the dye component.

E010: A kit according to E008-009, wherein the dye component comprises from 0.2 to 2% of the alkalizing agent, by total weight of the dye component.

E011: A kit according to E008-010, wherein the dye component comprises from 0.2 to 1% of the alkalizing agent, by total weight of the dye component.

E012: A kit according to E008-011, wherein the dye component comprises from 0.6 to 0.9% of the alkalizing agent, by total weight of the dye component.

E013: A kit according to E008-012, wherein the alkalizing agent is chosen from ammonia, alkanolamines, alkali metals and ammonium hydroxides, alkali metal and ammonium carbonates, and mixtures thereof E014: A kit according to E008-013, wherein the alkalizing agent is chosen from ammonia, monoethanolamine, sodium hydroxide, and mixtures thereof.

E015: A kit according to E008-014, wherein the alkalizing agent is a mixture of monoethanolamine and sodium hydroxide.

E016: A kit according to E001-015, wherein the dye component comprises at least one chelant.

E017: A kit according to E016, wherein the dye component comprises from 1.2 to 1.8% of the chelant, by total weight of the dye component.

E018: A kit according to E016-017, wherein the dye component comprises from 1.2 to 1.6% of the chelant, by total weight of the dye component.

E019: A kit according to E016-018, wherein the dye component comprises about 1.4% of the chelant, by total weight of the dye component.

E020: A kit according to E016-019, wherein the chelant is chosen from carboxylic acids, phosphonic acids, polyphosphoric acids, their salts thereof, and mixtures thereof.

E021: A kit according to E016-020, wherein the chelant is chosen from aminocarboxylic acids.

E022: A kit according to E016-021, wherein the chelant is chosen from DTPA, EDDS, EDGA, HPDS, GADS, EDDG, HPDDS, EDTA, EDC, EDDHA, DDS, HBED, their salts thereof, and mixtures thereof.

E023: A kit according to E016-022, wherein the chelant is chosen from EDDS, EDTA, their salts thereof, and mixtures thereof.

E024: A kit according to E016-023, wherein the chelant is a mixture of EDDS and EDTA.

E025: A kit according to E001-024, wherein the dye component comprises at least one buffering acidic compound.

E026: A kit according to E025, wherein the dye component comprises from 0.01 to % of the buffering acidic compound, by total weight of the dye component.

E027: A kit according to E025-026, wherein the dye component comprises from 0.05 to 0.45% of the buffering acidic compound, by total weight of the dye component.

E028: A kit according to E025-027, wherein the dye component comprises from 0.15 to 0.45% of the buffering acidic compound, by total weight of the dye component.

E029: A kit according to E025-028, wherein the buffering acidic compound is citric acid.

E030: A kit according to E001-029, wherein the dye component comprises at least one anionic surfactant.

E031: A kit according to E030, wherein the dye component comprises from 0.2 to 1% of the anionic surfactant, by total weight of the dye component.

E032: A kit according to E030-031, wherein the dye component comprises from 0.5 to 0.8% of the anionic surfactant, by total weight of the dye component.

E033: A kit according to E030-032, wherein the dye component comprises from 0.5 to 0.65% of the anionic surfactant, by total weight of the dye component.

E034: A kit according to E030-033, wherein the anionic surfactant is chosen from C14 to C30 alkyl phosphates, C14 to C30 alkyl ether phosphates, and mixtures thereof.

E035: A kit according to E030-034, wherein the anionic surfactant is chosen from C14 to C18 alkyl phosphates, C14 to C18 alkyl ether phosphates, and mixtures thereof.

E036: A kit according to E030-035, wherein the anionic surfactant is a mixture of dicetyl phosphate and ceteth-10 phosphate.

E037: A kit according to E001-036, wherein the dye component comprises at least one fatty alcohol.

E038: A kit according to E037, wherein the dye component comprises from 1.6 to 2.5% of at least one fatty alcohol, by total weight of the dye component.

E039: A kit according to E037-038, wherein the dye component comprises from 1.6 to 2.3% of at least one fatty alcohol, by total weight of the dye component.

E040: A kit according to E037-039, wherein the dye component comprises from 1.65 to 2.1% of at least one fatty alcohol, by total weight of the dye component.

E041: A kit according to E037-040, wherein the fatty alcohol is chosen from linear or branched C14 to C30 fatty alcohols.

E042: A kit according to E037-041, wherein the fatty alcohol is chosen from cetyl alcohol, stearyl alcohol, cetostearyl alcohol, cetearyl alcohol, behenyl alcohols, and mixtures thereof.

E043: A kit according to E037-042, wherein the fatty alcohol is cetearyl alcohol.

E044: A kit according to E001-043, wherein the dye component comprises at least one non-ionic surfactant.

E045: A kit according to E044, wherein the dye component comprises from 0.1 to 0.5% of the non-ionic surfactant, by total weight of the dye component.

E046: A kit according to E044-045, wherein the dye component comprises from 0.2 to 0.3% of the non-ionic surfactant, by total weight of the dye component.

E047: A kit according to E044-046, wherein the dye component comprises about 0.25% of the non-ionic surfactant, by total weight of the dye component.

E048: A kit according to E044-047, wherein the non-ionic surfactant is chosen from polyoxyethylene C14 to C30 alkyl ethers.

E049: A kit according to E044-048, wherein the non-ionic surfactant is chosen from polyoxyethylene C14 to C30 alkyl ethers, comprising one or more polyethyleneoxide chains having at least 50.

E050: A kit according to E044-049, wherein the non-ionic surfactant is chosen from steareth-20; steareth-100, steareth-150, steareth-200, and mixtures thereof E051: A kit according to E044-050, wherein the non-ionic surfactant is steareth-200.

E052: A kit according to E001-051, wherein the dye component comprises at least one oxidative hair dye precursor and at least one coupler.

E053: A kit according to E052, wherein the dye component comprises from 20% or less of the oxidative hair dye precursor and the coupler.

E054: A kit according to E052-053, wherein the dye component comprises from 0.002 to 20% of the oxidative hair dye precursor and the coupler.

E055: A kit according to E052-054, wherein the dye component comprises from 0.002 to 10% of the oxidative hair dye precursor and the coupler.

E056: A kit according to E052-055, wherein the dye component comprises from 0.02 to 4% of the oxidative hair dye precursor and the coupler.

E057: A kit according to E052-056, wherein the dye component comprises from 0.4 to 2% of the oxidative hair dye precursor and the coupler.

E058: A kit according to E052-057, wherein the oxidative hair dye precursor is chosen from chosen from toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxy ethyl)-p-phenylenediamine, 2,2'-(2-(4-aminophenylamino)ethylazanediyl) diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-tri amino-4-pyrimidinol, 1-hydroxyethyl-4,5-di-aminopyrazol e sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1 (5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy]ethanol hydrochloride, salts thereof, and mixtures thereof.

E059: A kit according to E052-058, wherein the coupler is chosen from resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-2-amino-5-phenylphenol, 2-amino-5-methylphenol, 2-amino-6-methylphenol, 2-amino-5-ethoxyphenol, 5-methyl-2-(methylamino) phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl) diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5 (41-1)-one, 1,2,4-trihydroxybenzene, 2-(benzo[d][1,3]dioxol-5-ylamino)ethanol, and mixtures thereof.

E060: A kit according to E001-059, wherein the dye component comprises at least one solvent.

E061: A kit according to E060, wherein the dye component comprises at least 50% of the solvent, by total weight of the dye component.

E062: A kit according to E060-061, wherein the dye component comprises at least 60% of the solvent, by total weight of the dye component.

E063: A kit according to E060-062, wherein the dye component comprises at least 70% of the solvent, by total weight of the dye component.

E064: A kit according to E060-063, wherein the solvent is chosen from water, or a mixture of water and at least one organic solvent.

E065: A kit according to E064, wherein the organic solvent is chosen from C1 to C4 lower alkanols, aromatic alcohols, polyols and polyol ethers, propylene carbonates and mixtures thereof.

E066: A kit according to E064-065, wherein the organic solvent is chosen from ethanol, propanol, isopropanol, glycerol, 1,2-propylene glycol, hexylene glycol, ethoxy diglycol, and mixtures thereof E067: A kit according to E064-066, wherein the organic solvent is propylene glycol.

E068: A kit according to E060-067, wherein the solvent is a mixture of water and at least one organic solvent.

E069: A kit according to E060-068, wherein the solvent is a mixture of water and propylene glycol.

E070: A kit according to E001-069, wherein the dye component comprises at least one thickener.

E071: A kit according to E070, wherein the dye component comprises at least 0.1% of the thickener, by total weight of the dye component.

E072: A kit according to E070-071, wherein the dye component comprises from 0.1% to 2.0% of the thickener, by total weight of the dye component.

E073: A kit according to E070-072, wherein the dye component comprises about 0.15% of the thickener, by total weight of the dye component.

E074: A kit according to E070-073, wherein the thickener is chosen from associative polymers, polysaccharides, non-associative polycarboxylic polymers, and mixtures thereof E075: A kit according to E070-074, wherein the thickener is chosen from polysaccharides.

E076: A kit according to E070-075, wherein the thickener is xantham gum.

E077: A kit according to E001-076, wherein the dye component comprises at least one radical scavenger E078: A kit according to E001-077, wherein the dye component comprises at least one conditioning agent.

E079: A kit according to E001-078, wherein the dye component comprises at least one direct dye.

E080: A kit according to E079, wherein the dye component comprises less than 4% of the direct dye, by total weight of the dye component.

E081: A kit according to E001-080, wherein the dye component comprises at least one other ingredient.

E082: A kit according to E081, wherein the dye component comprises 7% or less of the other ingredient, by total weight of the dye component.

E083: A kit according to E081-082, wherein the dye component comprises from 0.01 to 7% of the other ingredient, by total weight of the dye component.

E084: A kit according to E081-083, wherein the other ingredient is chosen from additional anionic surfactants, cationic surfactants, nonionic surfactants, amphoteric surfactants, zwitterionic surfactants, non-thickening viscosity (rheology) modifiers, fragrances, enzymes, dispersing agents, peroxide stabilizing agents, antioxidants, natural ingredients, ceramides, preserving agents, opacifiers and pearling agents, and mixtures thereof.

E085: A kit according to E001-084, wherein the dye component comprises at least one non-thickening viscosity (rheology) modifier.

E086: A kit according to E001-085, wherein the dye component comprises at least one additional anionic surfactant.

E087: A kit according to E001-086, wherein the dye component comprises at least one antioxidant.

E088: A kit according to E001-087, wherein the oxidative component comprises at least one oxidizing agent.

E089: A kit according to E088, wherein the oxidative component comprises from 1 to 3% of the oxidizing agent, by total weight of the oxidizing component.

E090: A kit according to E088-089, wherein the oxidative component comprises from 1.2 to 2.4% of the oxidizing agent, by total weight of the oxidizing component.

E091: A kit according to E088-090, wherein the oxidative component comprises from 1.5 to 2% of the oxidizing agent, by total weight of the oxidizing component.

E092: A kit according to E088-091, wherein the oxidizing component is chosen from water-soluble inorganic peroxygen materials capable of yielding hydrogen peroxide in an aqueous solution.

E093: A kit according to E088-092, wherein the oxidizing component is chosen from hydrogen peroxide, inorganic alkali metal peroxides, organic peroxides, inorganic perhydrate salt bleaching compounds, and mixtures thereof.

E094: A kit according to E088-093, wherein the oxidizing component is chosen from hydrogen peroxide, persulphates, and mixtures thereof.

E095: A kit according to E088-094, wherein the oxidizing component is hydrogen peroxide.

E096: A kit according to E001-095, wherein the oxidative component comprises at least one buffering acidic compound.

E097: A kit according to E096, wherein the oxidative component comprises from 0.15 to 0.5% of the buffering acidic compound, by total weight of the oxidative component.

E098: A kit according to E096-097, wherein the oxidative component comprises from 0.17 to 0.4% of the buffering acidic compound, by total weight of the oxidative component.

E099: A kit according to E096-098, wherein the oxidative component comprises from 0.17 to 0.3% of the buffering acidic compound, by total weight of the oxidative component.

E100: A kit according to E096-099, wherein the buffering acidic compound is phosphoric acid.

E101: A kit according to E001-100, wherein the oxidative component comprises at least one buffering alkali compound.

E102: A kit according to E101, wherein the oxidative component comprises from 0.2 to 0.6% of the buffering alkali compound, by total weight of the oxidative component.

E103: A kit according to E101-102, wherein the oxidative component comprises from 0.2 to 0.5% of the buffering alkali compound, by total weight of the oxidative component.

E104: A kit according to E101-103, wherein the oxidative component comprises from 0.2 to 0.35% of the buffering alkali compound, by total weight of the oxidative component.

E105: A kit according to E101-104, wherein the buffering alkali compound is disodium phosphate.

E106: A kit according to E001-105, wherein the oxidative component comprises at least one fatty alcohol.

E107: A kit according to E106, wherein the oxidative component comprises from 1.6 to 3.4% of at least one fatty alcohol, by total weight of the oxidative component.

E108: A kit according to E106-107, wherein the oxidative component comprises from 1.8 to 3.2% of at least one fatty alcohol, by total weight of the oxidative component.

E109: A kit according to E106-108, wherein the oxidative component comprises from 2 to 3% of at least one fatty alcohol, by total weight of the oxidative component.

E110: A kit according to E106-109, wherein the fatty alcohol is chosen from linear or branched C14 to C30 fatty alcohols.

E111: A kit according to E106-110, wherein the fatty alcohol is chosen from cetyl alcohol, stearyl alcohol, cetostearyl alcohol, cetearyl alcohol, behenyl alcohols, and mixtures thereof.

E112: A kit according to E106-111, wherein the fatty alcohol is cetearyl alcohol.

E113: A kit according to E001-112, wherein the oxidative component comprises at least one chelant.

E114: A kit according to E113, wherein the oxidative component comprises 0.1% or less of the chelant, by total weight of the oxidative component.

E115: A kit according to E113-114, wherein the oxidative component comprises from 0.005 to 0.05% of the chelant, by total weight of the oxidative component.

E116: A kit according to E113-115, wherein the oxidative component comprises about 0.01% of the chelant, by total weight of the oxidative component.

E117: A kit according to E113-116, wherein the chelant is etidronic acid.

E118: A kit according to E001-117, wherein the oxidative component comprises at least one solvent.

E119: A kit according to E118, wherein the oxidative component comprises at least 50% of the solvent, by total weight of the oxidative component.

E120: A kit according to E118-119, wherein the oxidative component comprises at least 60% of the solvent, by total weight of the oxidative component.

E121: A kit according to E118-120, wherein the oxidative component comprises at least 70% of the solvent, by total weight of the oxidative component.

E122: A kit according to E118-121, wherein the solvent is chosen from water, or a mixture of water and at least one organic solvent.

E123: A kit according to E118-122, wherein the organic solvent is chosen from C1 to C4 lower alkanols, aromatic alcohols, polyols and polyol ethers, propylene carbonate, and mixtures thereof.

E124: A kit according to E118-123, wherein the organic solvent is chosen from ethanol, propanol, isopropanol, glycerol, 1,2-propylene glycol, hexylene glycol, ethoxy diglycol, and mixtures thereof.

E125: A kit according to E118-124, wherein the organic solvent is propylene glycol.

E126: A kit according to E118-125, wherein the solvent is water.

E127: A kit according to E001-0126, wherein the oxidative component comprises at least one conditioning agent.

E128: A kit according to E127, wherein the oxidative component comprises 40% or less of the conditioning agent, by total weight of the oxidative component.

E129: A kit according to E127-128, wherein the oxidative component comprises from 0.1 to 40% of the conditioning agent, by total weight of the oxidative component.

E130: A kit according to E127-129, wherein the oxidative component comprises from 0.2 to 30% of the conditioning agent, by total weight of the oxidative component.

E131: A kit according to E127-130, wherein the oxidative component comprises from 0.4 to 20% of the conditioning agent, by total weight of the oxidative component.

E132: A kit according to E127-131, wherein the oxidative component comprises from 0.4% to 10% of the conditioning agent, by total weight of the oxidative component.

E133: A kit according to E127-132, wherein the oxidative component comprises about 3.3% of the conditioning agent, by total weight of the oxidative component.

E134: A kit according to E127-133, wherein the conditioning agent is chosen from polyhydric alcohols, silicone materials, amino silicones, fatty alcohols, polymeric resins, polyol carboxylic acid esters, cationic polymers, cationic surfactants, insoluble oils, oil-derived materials, mineral oil, and mixtures thereof.

E135: A kit according to E127-134, wherein the conditioning agent is mineral oil.

E136: A kit according to E001-135, wherein the oxidative component comprises at least one direct dye.

E137: A kit according to E36, wherein the oxidative component comprises less than 4% of the direct dye, by total weight of the oxidative component.

E138: A kit according to E001-137, wherein the oxidative component comprises at least one thickener.

E139: A kit according to E138, wherein the oxidative component comprises 0.1% or less of the thickener, by total weight of the oxidative component.

E140: A kit according to E138-139, wherein the oxidative component comprises from 0.001% to 0.1% of the thickener, by total weight of the oxidative component.

E141: A kit according to E138-140, wherein the thickener is chosen from associative polymers, polysaccharides, non-associative polycarboxylic polymers, and mixtures thereof.

E142: A kit according to E138-141, wherein the thickener is chosen from associative polymers.

E143: A kit according to E001-142, wherein the oxidative component comprises at least one other ingredient.

E144: A kit according to E143, wherein the oxidative component comprises 5% or less of the other ingredient, by total weight of the oxidative component.

E145: A kit according to E143-144, wherein the oxidative component comprises from 0.01 to 5% of the other ingredient, by total weight of the oxidative component.

E146: A kit according to E143-145, wherein the other ingredient is chosen from additional anionic, cationic, non-ionic, amphoteric or zwitterionic surfactants, non-thickening viscosity (rheology) modifiers, fragrances, enzymes, dispersing agents, peroxide stabilizing agents, antioxidants, natural ingredients, ceramides, preserving agents, opacifiers and pearling agents, and mixtures thereof.

E147: A kit according to E001-146, wherein the oxidative component comprises at least one peroxide stabilizing agent.

E148: A hair coloring composition, obtained by mixing a dye component and an oxidative component, according to E001-147, wherein the composition has a pH from 6.8 to 8, preferably 7.2 to 7.99 (immediately upon mixing).

E149: A hair coloring composition, according to E148, wherein the composition comprises at least one alkalizing agent.

E150: A hair coloring composition, according to E149, wherein the composition comprises from 0.1 to 2% of the alkalizing agent, by total weight of the composition.

E151: A hair coloring composition, according to E148-150, wherein the composition comprises at least one oxidizing agent.

E152: A hair coloring composition, according to E151, wherein the composition comprises from 0.5 to 1.5% of the oxidizing agent, by total weight of the composition.

E153: A hair coloring composition, according to E148-152, wherein the composition comprises at least one chelant.

E154: A hair coloring composition, according to E153, wherein the composition comprises from 0.6 to 0.9% of the chelant, by total weight of the composition.

E155: A hair coloring composition, according to E148-154, wherein the composition comprises at least a first buffering acidic compound.

E156: A hair coloring composition, according to E155, wherein the composition comprises from 0.05 to 0.3% of the first buffering acidic compound, by total weight of the composition.

E157: A hair coloring composition, according to E155-156, wherein the first buffering acidic compound is citric acid.

E158: A hair coloring composition, according to E148-157, wherein the composition comprises at least a second buffering acidic compound.

E159: A hair coloring composition, according to E158, wherein the composition comprises from 0.075 to 0.25% of the second buffering acidic compound, by total weight of the composition.

E160: A hair coloring composition, according to E158-159, wherein the second buffering acidic compound is phosphoric acid.

E161: A hair coloring composition, according to E148-160, wherein the composition comprises at least one buffering alkali compound.

E162: A hair coloring composition, according to E161, wherein the composition comprises from 0.1 to 0.3% of the buffering alkali compound, by total weight of the composition.

E163: A hair coloring composition, according to E161-162, wherein the buffering alkali compound is disodium phosphate.

E164: A hair coloring composition, according to E148-163, wherein the composition comprises a gel network thickener system.

E165: A hair coloring composition, according to E164, wherein the gel network thickener system comprises at least one anionic surfactant, at least one fatty alcohol and at least one non-ionic surfactant E166: A hair coloring composition, according to E164-165, wherein the composition comprises from 1.2 to 4.5% of the gel network system, by total weight of the composition.

E167: A hair coloring composition, according to E148-166, wherein the composition comprises at least one oxidative hair dye precursor and at least one coupler.

E168: A hair coloring composition, according to E167, wherein the composition comprises the oxidative hair dye precursor and the coupler altogether in an amount of 10% or less, by total weight of the composition.

E169: A hair coloring composition, according to E148-168, wherein the composition comprises at least one solvent.

E170: A hair coloring composition, according to E169, wherein the composition comprises from at least 50% of the solvent, by total weight of the composition.

E171: A hair coloring composition, according to E148-170, wherein the composition comprises at least one radical scavenger.

E172: A hair coloring composition, according to E148-171, wherein the composition comprises at least one conditioning agent.

E173: A hair coloring composition, according to E148-172, wherein the composition comprises at least one direct dye.

E174: A hair coloring composition, according to E148-173, wherein the composition comprises at least one second chelant.

E175: A hair coloring composition, according to E148-174, wherein the composition comprises at least one thickener.

E176: A hair coloring composition, according to E148-175, wherein the composition comprises at least one other ingredient.

E177: A hair coloring composition, according to E176, wherein the other ingredient is chosen from additional anionic, cationic, nonionic, amphoteric or zwitterionic surfactants, non-thickening viscosity (rheology) modifiers, fragrances, enzymes, dispersing agents, peroxide stabilizing agents, antioxidants, natural ingredients, ceramides, preserving agents, opacifiers and pearling agents, and mixtures thereof E178: A method of treating hair with the hair coloring composition, according to E148-177.

E179: A method of treating hair, according to E178, wherein the method comprises the step of providing the dye component and the oxidative component, according to E001-148.

E180: A method of treating hair, according to E178-179, wherein the method comprises the step of mixing the oxidative component and the dye component to obtain a hair coloring composition.

E181: A method of treating hair, according to E178-180, wherein the method comprises the step of applying the hair coloring composition for the oxidative dyeing of keratin fibers onto the hair.

E182: A method of treating hair, according to E178-181, wherein the method comprises the step of leaving the composition on the hair for from 2 to 60 minutes.

E183: A method of treating hair, according to E178-182, wherein the method comprises the step of rinsing the composition from the hair.

E184: A use of the hair coloring composition, obtained by mixing a dye component and an oxidative component, according to E001-177, for maintaining natural strand-to-strand variation.

E185: A use of the hair coloring composition, obtained by mixing a dye component and an oxidative component, according to E001-177, for providing an enhanced root-to-tip evenness on hair.

CLAUSES

Clause 1: A hair coloring composition comprising, by total weight of the composition: at least one oxidizing agent present in an amount from 0.5 to 1.5% by weight; at least one chelant present in an amount from 0.6 to 0.9% by weight; at least one buffering acidic compound present in an amount from 0.01 to 0.4% by weight and at least one buffering alkali compound present in an amount from 0.01 to 0.4% by weight, wherein the buffering acidic compound and the buffering alkali compound form a buffering system; a gel network thickener system present in an amount from 1.2 to 4.5% by weight; wherein the gel network thickener system comprises at least one anionic surfactant, at least one fatty alcohol and at least one non-ionic surfactant; at least one alkalizing agent present in an amount from 0.1 to 2% by weight; at least one oxidative hair dye precursor and at least one coupler present altogether in an amount from 0.001 to 10% by weight; at least one solvent present in an amount of at least 50% by weight; and wherein the composition comprises a pH from 6 to 8.

Clause 2: A hair coloring composition, according to clause 1, comprising, by total weight of the composition: from 0.8 to 1.2% by weight of the oxidizing agent; from 0.6 to by weight of the chelant; from 0.05 to 0.4% by weight of the buffering acidic compound and from 0.05 to 0.3% by weight of the buffering alkali compound; from 0.5 to 1% by weight of the anionic surfactant, from 0.8 to 3.5% by weight of the fatty alcohol and from 0.05 to 0.25% by weight the non-ionic surfactant; from 0.1% to 1% by weight of the alkalizing agent; from 0.001 to 5% by weight of the mixture of the oxidative hair dye precursor and the coupler; at least 60% by weight of the solvent; and wherein the composition comprises a pH from 6.8 to 7.99.

Clause 3: A hair coloring composition, according to any preceding clauses, wherein: the oxidizing agent is a water-soluble inorganic peroxygen material; preferably the oxidizing agent is chosen from hydrogen peroxide, persulphates and mixtures thereof; the chelant is chosen from aminocarboxylic acids; preferably from ethylenediamine disuccinic acid, ethylenediaminetetraacetic acid, and mixture thereof; the buffering acidic compound is chosen from phosphoric acid, citric acid and mixtures thereof and the buffering alkali compound is chosen from disodium phosphate, potassium chloride and mixtures thereof; the anionic surfactant is chosen alkyl ether phosphates have an average of from 1 to 20 ethylene oxide units; the fatty alcohol is chosen from cetyl alcohol, stearyl alcohol, cetostearyl alcohol, cetearyl alcohol, behenyl alcohols and mixtures thereof; and the non-ionic surfactant is chosen steareth-20, steareth-100, steareth-150, steareth-200 and mixtures thereof; the alkalizing agent is chosen from ammonia, monoethanolamine, their derivatives thereof, and mixtures thereof; preferably the alkalizing agent is monoethanolamine and its derivatives thereof; the solvent is chosen from water, or a mixture of water and at least one organic solvent.

Clause 4: The composition, according to any preceding clauses, comprises an additional ingredient chosen from at least one radical scavenger, at least one conditioning agent, at least one direct dye, at least one thickener and/or rheology modifier and mixtures thereof.

Clause 5: The composition, according to any preceding clauses, wherein the composition is obtained by mixing a dye component and an oxidative component in a weight ratio from 3:1 to 1:3.

Clause 6: A kit for obtaining a hair coloring composition, according to any preceding clauses, comprising at least one dye component, at least one oxidative component, optionally at least one conditioning component, optionally a pre-treatment composition and/or optionally a colour refresher composition.

Clause 7: A method of treating hair comprising the steps of: providing a dye component as described herein; providing an oxidative component as described herein; mixing the oxidative component and the dye component to obtain a hair coloring composition as described herein; applying the hair coloring composition for the oxidative dyeing of keratin fibers onto the hair; leaving the composition on the hair for from 2 to 60 minutes; and rinsing the composition from the hair.

The invention claimed is:

1. A kit comprising a dye component and an oxidative component, for obtaining a hair coloring composition upon the mixing of the dye component and the oxidative component in a weight ratio from 3:1 to 1:3, wherein the hair coloring composition has a pH of about 7.2 to 7.9 upon mixing and a pH of about 6.5 to 7 after at least about 20 minutes post mixing;

wherein the dye component has a pH from 8.5 to 10, and comprises, by total weight of the dye component:
at least one alkalizing agent present in an amount from 0.2 to 4%;
a chelant mixture of EDTA and EDDS present in an amount of the mixture of from 1.2 to 1.8%;
at least one buffering acidic compound present in an amount from 0.01 to 0.6%; wherein the buffering acidic compound is citric acid;
at least one anionic surfactant present in an amount from 0.2 to 1%;
at least one fatty alcohol present in an amount from 1.6 to 2.5%;
at least one non-ionic surfactant present in an amount from 0.1 to 0.5%;
at least one oxidative hair dye precursor and at least one coupler present altogether in an amount of 20% or less; and
at least one solvent present in an amount from at least 50%; and wherein the oxidative component has a pH from 1.8 to 3.5, and comprises, by total weight of the oxidative component:
at least one oxidizing agent present in an amount from 1 to 3%;
at least one buffering acidic compound present in an amount from 0.15 to 0.5%; wherein the buffering acidic compound is phosphoric acid;
at least one buffering alkali compound present in an amount from 0.2 to 0.6%; wherein the buffering alkali compound is disodium phosphate; and
wherein the % of phosphoric acid is lower than or equal to the % of disodium phosphate; and
at least one solvent present in an amount from at least 50%.

2. The kit according to claim 1;
wherein the dye component has a pH from 9 to 10, and wherein it comprises, by total weight of the dye component:
the alkalizing agent present in an amount from 0.2 to 2%,
the chelant mixture of EDTA and EDDS is present in an amount from 1.2 to 1.6%;
the buffering acidic compound present in an amount from 0.05 to 0.45%,
the anionic surfactant present in an amount from 0.5 to 0.8%, the fatty alcohol present in an amount from 1.6 to 2.3%,
the non-ionic surfactant present in an amount from 0.2 to 0.3%,
the oxidative hair dye precursor and at least one coupler present altogether in an amount from 0.002 to 20%, and
the solvent present in an amount from at least 60%
wherein the oxidative component has a pH from 2 to 3, and wherein it comprises, by total weight of the oxidative component:
the solvent present in an amount from at least 60%,
the oxidizing agent present in an amount from 1.2 to 2.4%,
the buffering acidic compound present in an amount from 0.17 to 0.4%,
the buffering alkali compound present in an amount from 0.2 to 0.5%; and
the solvent present in an amount from at least 60%.

3. The kit according to claim 1 wherein: the alkalizing agent, present in the dye component, is chosen from ammonia, alkanolamines, alkali metals and ammonium hydroxides, alkali metal and ammonium carbonates, and mixtures thereof;
the buffering acidic compound, present in the dye component, is citric acid;
the anionic surfactant, present in the dye component, is chosen from C14 to C30 alkyl phosphates, C14 to C30 alkyl ether phosphates, and mixtures thereof;
the fatty alcohol, present in the dye component, is chosen from linear or branched C14 to C30 fatty alcohols:
the non-ionic surfactant, present in the dye component, is chosen from polyoxyethylene C14 to C30 alkyl ethers:
the oxidative hair dye precursor, present in the dye component, is chosen from toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino) ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino) phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexyl pyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy]ethanol hydrochloride, salts thereof, and mixtures thereof; and
the coupler is chosen from resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethyl phenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino) phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-(phenylene) bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, pyridine-2,6-diol, 5,6-dihydroxyindole, 6-hydroxyindiole, 3-methyl-1-phenyl-1H-pyrazol-5(4H)-one, 1,2,4-trihydroxybenxine, 2-(benzo[d][1,3]dioxol-5-ylamino)ethanol, and mixtures thereof;
the solvent, present in the dye component, is chosen from water, or a mixture of water and at least one organic solvent,
the oxidizing agent, present in the oxidative component, is chosen from water-soluble inorganic peroxygen materials capable of yielding hydrogen peroxide in an aqueous solution;
and
the solvent is chosen from water, or a mixture of water and at least one organic solvent.

4. The kit according to claim 1 wherein the dye component further comprises at least one radical scavenger, at least one conditioning agent, at least one direct dye, and/or at least one thickener.

5. The kit according to claim 1 wherein the oxidative component further comprises at least one chelant as etidronic acid, at least one fatty alcohol, at least one conditioning agent, at least one direct dye, and/or at least one thickener.

6. The kit according to claim 1 wherein the dye component and/or the oxidative component comprises at least one other ingredient chosen from additional anionic surfactants, cationic surfactants, nonionic surfactants, amphoteric surfactants, zwitterionic surfactants, non-thickening viscosity (rheology) modifiers, fragrances, enzymes, dispersing agents, peroxide stabilizing agents, antioxidants, natural ingredients, ceramides, preserving agents, opacifiers and pearling agents, and mixtures thereof.

7. A hair coloring composition having a pH from 7.2 to 7.99, wherein the hair coloring composition comprises, by total weight of the composition:
at least one alkalizing agent present in an amount from 0.1 to 2%;
at least one oxidizing agent present in an amount from 0.5 to 1.5%;
a chelant mixture of EDTA and EDDS wherein the mixture is present in an amount from 0.6 to 0.9%;
at least a first buffering acidic compound present in an amount from 0.05 to 0.3%,
wherein the first buffering acidic compound is citric acid;
at least a second buffering acidic compound present in an amount from 0.075 to 0.25%, wherein the second buffering acidic compound is phosphoric acid;
at least one buffering alkali compound present in an amount from 0.1 to 0.3%, wherein the buffering alkali compound is disodium phosphate, wherein the % of phosphoric acid is lower than or equal to the % of disodium phosphate;

a gel network thickener system present in an amount from 1.2 to 4.5%, wherein the gel network thickener system comprises at least one anionic surfactant, at least one fatty alcohol and at least one non-ionic surfactant;

at least one oxidative hair dye precursor and at least one coupler present altogether in an amount of 10% or less; and at least one solvent present in an amount from at least 50%, and;

wherein the pH of the hair coloring composition reduces to a pH of about 6.5 to 7 in at least about 20 minutes after formation.

8. The hair coloring composition according to claim 7, wherein it further comprises at least one radical scavenger, at least one conditioning agent, at least one direct dye, at least one second chelant and/or at least one thickener.

9. The hair coloring composition according to claim 7, wherein it further comprises at least one other ingredient chosen from additional anionic surfactants, cationic surfactants, nonionic surfactants, amphoteric surfactants, zwitterionic surfactants, non-thickening viscosity (rheology) modifiers, fragrances, enzymes, dispersing agents, peroxide stabilizing agents, antioxidants, natural ingredients, ceramides, preserving agents, opacifiers and pearling agents, and mixtures thereof.

10. A method of treating hair comprising the steps of: providing the dye component and the oxidative component according to claim 1;

mixing the oxidative component and the dye component in a weight ratio from 3:1 to 1:3, to obtain a hair coloring composition having a pH from 7.2 to 7.99;

applying the hair coloring composition for the oxidative dyeing of keratin fibers onto the hair;

leaving the composition on the hair from 2 to 60 minutes, wherein the composition has a pH which over development time on hair drops to 6.5-7.0; and rinsing the composition from the hair.

11. The method according to claim 10, wherein the composition has a pH which drops to 6.5 to 7.0 after 20 minutes.

12. The method according to claim 10 wherein the treating maintains natural strand-to-strand variation.

13. The method according to claim 10 wherein the treating provides an enhanced root-to-tip evenness on hair.

14. The method according to claim 10 wherein the treating reduces hair damage without compromising color result.

15. The hair coloring composition according to claim 1, wherein the composition is obtained by mixing the dye component and the oxidative component in a weight ratio from 2:1 to 1:2.

16. The hair coloring composition, according, to claim 1, wherein the composition is obtained by mixing the dye component and the oxidative component in a weight ratio of 1:1.

* * * * *